(12) United States Patent
Breitbart et al.

(10) Patent No.: US 8,999,960 B2
(45) Date of Patent: Apr. 7, 2015

(54) OXIDIZED THIOPHOSPHOLIPID COMPOUNDS AND USES THEREOF

(75) Inventors: Eyal Breitbart, Hashmonaim (IL); Eti Kovalevski-Ishai, Netania (IL); Erez Feige, Hemed (IL); Itzhak Mendel, Rechovot (IL); Zeev Ziniuk, Rechovot (IL); Gideon Halperin, Har-Adar (IL)

(73) Assignee: Vascular Biogenics Ltd., Or Yehuda (IL)

(*) Notice: Subject to any disclaimer, the term of this patent is extended or adjusted under 35 U.S.C. 154(b) by 116 days.

(21) Appl. No.: 13/122,766

(22) PCT Filed: Oct. 1, 2009

(86) PCT No.: PCT/IL2009/000949
§ 371 (c)(1),
(2), (4) Date: Apr. 6, 2011

(87) PCT Pub. No.: WO2010/041242
PCT Pub. Date: Apr. 15, 2010

(65) Prior Publication Data
US 2011/0195937 A1    Aug. 11, 2011

Related U.S. Application Data

(60) Provisional application No. 61/103,571, filed on Oct. 8, 2008.

(51) Int. Cl.
C07F 9/10      (2006.01)
C07F 9/165     (2006.01)
A61K 31/661    (2006.01)
A61P 37/06     (2006.01)

(52) U.S. Cl.
CPC ..................... C07F 9/10 (2013.01)

(58) Field of Classification Search
None
See application file for complete search history.

(56) References Cited

U.S. PATENT DOCUMENTS

| | | | |
|---|---|---|---|
| 4,543,258 A | 9/1985 | Urata et al. | |
| 6,838,452 B2 | 1/2005 | Harats et al. | |
| 7,186,704 B2 | 3/2007 | Harats et al. | |
| 7,504,388 B2 | 3/2009 | Harats et al. | |
| 7,625,882 B2 | 12/2009 | Harats et al. | |
| 7,807,847 B2 | 10/2010 | Halperin et al. | |
| 7,893,291 B2 | 2/2011 | Harats et al. | |
| 7,902,176 B2 | 3/2011 | Harats et al. | |
| 7,973,023 B2 | 7/2011 | Harats et al. | |
| 8,124,800 B2 | 2/2012 | Halperin et al. | |
| 8,158,611 B2 | 4/2012 | Harats et al. | |
| 8,501,715 B2 | 8/2013 | Harats et al. | |
| 8,563,534 B2 | 10/2013 | Harats et al. | |
| 8,569,529 B2 | 10/2013 | Halperin et al. | |
| 2003/0225035 A1 | 12/2003 | Harats et al. | |
| 2007/0020691 A1 | 1/2007 | Kanter et al. | |
| 2007/0099868 A1 | 5/2007 | Harats et al. | |
| 2007/0112211 A1 | 5/2007 | Halperin et al. | |
| 2007/0264206 A1 | 11/2007 | Boga et al. | |
| 2008/0261865 A1 | 10/2008 | Harats et al. | |
| 2009/0074720 A1 | 3/2009 | Sabbadini | |
| 2011/0189212 A1 | 8/2011 | Harats et al. | |
| 2011/0207703 A1 | 8/2011 | Kovalevski-Ishai et al. | |
| 2012/0130108 A1 | 5/2012 | Halperin et al. | |
| 2012/0329757 A1 | 12/2012 | Harats et al. | |
| 2012/0329758 A1 | 12/2012 | Cohen et al. | |
| 2013/0079540 A1 | 3/2013 | Halperin et al. | |
| 2013/0158283 A1 | 6/2013 | Halperin et al. | |
| 2013/0172294 A1 | 7/2013 | Cohen et al. | |
| 2013/0190523 A1 | 7/2013 | Halperin et al. | |
| 2013/0203707 A1 | 8/2013 | Kovalevski-Ishai et al. | |
| 2013/0209555 A1 | 8/2013 | Sher et al. | |
| 2013/0225525 A1 | 8/2013 | Cohen et al. | |
| 2013/0237720 A1 | 9/2013 | Halperin et al. | |

FOREIGN PATENT DOCUMENTS

| | | |
|---|---|---|
| CA | 1102354 | 6/1981 |
| GB | 2 130 206 A | 5/1984 |
| JP | 54-41807 | 4/1979 |

(Continued)

OTHER PUBLICATIONS

Ottmann et al., caplus an 1967:284459.*
Nifant'ev et al., caplus an 1979:23434.*
Franklin et al., caplus an 2003:643618.*
Supplementary European Search Report and the European Search Opinion Dated Mar. 9, 2012 From the European Patent Office Re. Application No. 09824498.1.
International Preliminary Report on Patentability Dated May 19, 2011 From the International Bureau of WIPO Re. Application No. PCT/09/01049.
Examination Report Dated Nov. 21, 2011 From the Intellectual Property Office of New Zealand Re. Application No. 592357.

(Continued)

*Primary Examiner* — Sun Jae Yoo
(74) *Attorney, Agent, or Firm* — Sterne, Kessler, Goldstein & Fox, P.L.L.C.

(57) ABSTRACT

Novel oxidized thiophospholipids are provided herein, as well as methods for producing same, and uses thereof in treating or preventing an inflammation associated with endogenous oxidized lipids and related conditions. Exemplary oxidized thiophospholipid according to embodiments described herein have the formula:

$$\begin{array}{c} \text{O} - A_1 - X_1 \\ | \\ H_2C \\ \phantom{H_2C} \diagdown \\ \phantom{H_2C} \quad CH - O - A_2 - X_2 \\ \phantom{H_2C} \diagup \\ H_2C \quad \quad S \\ \phantom{H_2C} \quad \| \\ \phantom{H_2C} \quad O - P - B' \\ \phantom{H_2C} \quad \quad | \phantom{-} \diagdown \\ \phantom{H_2C} \quad \quad B'' \phantom{-} D' \\ \phantom{H_2C} \quad \quad \phantom{B''} \diagdown \\ \phantom{H_2C} \quad \quad \phantom{B''} \phantom{-} D'' \end{array}$$

wherein $X_1$, $X_2$, $A_1$, $A_2$, B', B", D' and D" are as described herein.

35 Claims, 2 Drawing Sheets

(56) References Cited

FOREIGN PATENT DOCUMENTS

| JP | 59-93022 | 5/1984 |
| JP | 59-175445 | 10/1984 |
| JP | 05-339387 | 12/1993 |
| JP | 08-059545 | 3/1996 |
| JP | 2005-505499 | 2/2005 |
| JP | 2008-037763 | 2/2008 |
| WO | WO 02/41827 A2 | 5/2002 |
| WO | WO 02/087465 A2 | 11/2002 |
| WO | WO 2004/106486 | 12/2004 |
| WO | WO 2006/006161 | 1/2006 |
| WO | WO 2008/084472 A2 | 7/2008 |
| WO | WO 2010/041242 | 4/2010 |
| WO | WO 2010/052718 | 5/2010 |
| WO | WO 2011/083465 A1 | 7/2011 |
| WO | WO 2011/083467 A1 | 7/2011 |
| WO | WO 2011/083469 A1 | 7/2011 |
| WO | WO 2013/033642 A1 | 3/2013 |
| WO | WO 2013/088245 A1 | 6/2013 |

OTHER PUBLICATIONS

International Search Report and the Written Opinion Dated Apr. 12, 2010 From the International Searching Authority Re.: Application No. PCT/09/00949.

International Search Report and the Written Opinion Dated Mar. 24, 2010 From the International Searching Authority Re.: Application No. PCT/09/01049.

Bochkov "Inflammatory Profile of Oxidized Phospholipids", Journal of Thrombosis and Haemastosis, 97: 348-354, Feb. 8, 2007.

Chen et al. "Polyunsaturated Phospholipids Promote the Oxidation and Fragmentation of γ-Hydroxyalkenals: Formation and Reactions of Oxidatively Truncated Ether Phospholipids", Journal of Lipid Research, 49: 832-846, Dec. 29, 2007.

Davies et al. "Oxidized Alkyl Phospholipids Are Specific, High Affinity Peroxisome Proliferator-Activated Receptor γ Ligands and Antagonists", The Journal of Biological Chemistry, 276(19): 16015-16023, May 11, 2001.

Invitation Pursuant to Rule 63(1) EPC Dated Feb. 3, 2012 From the European Patent Office Re. Application No. 09818874.1.

International Preliminary Report on Patentability Dated Apr. 21, 2011 From the International Bureau of WIPO Re. Application No. PCT/2009/000949.

Co-pending U.S. Appl. No. 13/520,719, filed Mar. 7, 2013, inventors Cohen, Y., et al.

Co-pending U.S. Appl. No. 13/709,198, filed Dec. 10, 2012, inventors Halperin, G. and Kovalevski-Ishai, E.

Co-pending U.S. Appl. No. 13/792,633, filed Mar. 11, 2013, inventors Sher, N., et al.

Co-pending U.S. Appl. No. 13/796,654, filed Mar. 12, 2013, inventors Halperin, G. and Kovalevski-Isahi, E.

Co-pending U.S. Appl. No. 13/828,643, filed Mar. 14, 2013, inventors Cohen, Y., et al.

Co-pending U.S. Appl. No. 13/828,883, filed Mar. 14, 2013, inventors Kovalevski-Ishai, E., et al.

Co-pending U.S. Appl. No. 13/833,940, filed Mar. 15, 2013, inventors Halperin, G. and Kovalevski-Ishai, E.

Rosario-Jansen, T., et al., "Phospholipids Chiral at Phosphorus. 13. Stereochemical Comparison of Phospholipase $A_2$, Lecithin-Cholesterol Acyl Transferase, and Platelet-Activating Factor," Phosphorus and Sulfur 30:601-604, Gordon and Breach Science Publishers, Inc., United Kingdom (1987).

Supplementary European Search Report for European Patent Applicaiton No. EP 09 81 8874, The Hague, Netherlands, mailed Jun. 28, 2013.

Bhattacharyya, S., et al., "Toll-Like Receptor 4 Signaling Augments Transforming Growth Factor-β Responses: A Novel Mechanism for Maintaining and Amplifying Fibrosis in Scleroderma," The American Journal of Pathology 182(1):192-205, Elsevier Inc., United States (2013).

Csak, T., et al., "Deficiency in myeloid differentiation factor-2 and toll-like receptor 4 expression attenuates nonalcoholic steatohepatitis and fibrosis in mice," Am J Physiol Gastrointest Liver Physiol 300:G433-G441, American Physiological Society, United States (Jan. 2011).

Abstract of Franklin, C., et al., "Design, Synthesis, and Evaluation of Water-Soluble Phospholipid Analogues as Inhibitors of Phospholipase C from Bacillus cereus," Journal of Organic Chemistry 68(19):7298-7307, American Chemical Society, United States (2003), Caplus AN 2003:643618.

Herre, J., et al., "Allergens as Immunomodulatory Proteins: The Cat Dander Protein Fel d 1 Enhances TLR Activation by Lipid Ligands," J Immunol 191:1529-1535, American Association of Immunologists, Inc., United States (2013).

Kwok, S-K., et al., "TLR2 litigation induces the production of IL-23/IL-17 via IL-6, STAT3 and NF-kB pathway in patients with primary Sjogren's syndrome," Arthritis Research & Therapy 14(R64):1-13, BioMed Central, England (2012).

Lartigue, A., et al., "Critical Role of TLR2 and TLR4 in Autoantibody Production and Glomerulonephritis in lpr Mutation-Induced Mouse Lupus," J Immunol 183:6207-6216, American Association of Immunologists, Inc., United States (2009).

Li, J., et al., "Toll-like receptors as therapeutic targets for autoimmune connective tissue diseases," Pharmacology & Therapeutics 138:441-451, Elsevier, Inc., England (2013).

Millien, V.O., et al., "Cleavage of Fibrinogen by Proteinases Elicits Allergic Responses Through Toll-Like Receptor 4," Science 341(6147):792-796, American Association for the Advancement of Science, United States (2013).

Miura, K., et al., "TLR2 and palmitic acid cooperatively contribute to the development of nonalcoholic steatohepatitis through inflammasome activation," Hepatology 57(2):577-589, Wiley, United States (2013).

Wen, Z., et al., "Autoantibody Induction by DNA-Containing Immune Complexes Requires HMGB1 with the TLR2/MicroRNA-155 Pathaway," J Immunol 190:5411-5422, American Association of Immunologists, Inc., United States (2013).

"Guidance for Industry: Estimating the Maximum Safe Starting Dose in Initial Clinical Trials for Therapeutics in Adult Healthy Volunteers," U.S. Department of Health and Human Services, Food and Drug Administration, Center for Drug Evaluation and Research, pp. 1-27 (Jul. 2005).

International Preliminary Report on Patentability for International Application No. PCT/IB2012/002930, International Bureau of WIPO, Geneva, Switzerland, issued Jun. 17, 2014.

U.S. Appl. No. 14/364,705, inventors Mendel, I., et al., national stage entry of International Application No. PCT/IB2012/002930, Int'l filing date: Dec. 11, 2012 (Not Published).

\* cited by examiner

OXIDIZED THIOPHOSPHOLIPID COMPOUNDS AND USES THEREOF

RELATED APPLICATIONS

This application is a National Phase of PCT Patent Application No. PCT/IL2009/000949 having International filing date of Oct. 1, 2009, which claims the benefit of priority of U.S. Provisional Patent Application No. 61/103,571 filed on Oct. 8, 2008. The contents of the above applications are all incorporated herein by reference.

FIELD AND BACKGROUND OF THE INVENTION

The present invention, in some embodiments thereof, relates to novel oxidized thiophospholipids and to methods employing oxidized thiophospholipids for treating or preventing an inflammation associated with endogenous oxidized lipids. The methods of the present embodiments can be utilized in treating or preventing inflammation associated diseases and disorders such as, for example, atherosclerosis and related disorders, autoimmune diseases or disorders, and proliferative diseases or disorders.

Oxidized phospholipids, including etherified derivatives, have been previously described as useful in the treatment of medical conditions such as, for example, cardiovascular diseases, cerebrovascular diseases and inflammatory diseases and disorders.

Thus, International Patent Application No. PCT/IL2004/000453 (Publication No. WO 04/106486) describes oxidized lipids for prevention and treatment of inflammation associated with endogenous oxidized lipids. An exemplary such compound is described and known as CI-201 (also referred to in the art as VB-201).

In addition, International Patent Application No. PCT/IL01/01080 (Publication No. WO 02/41827) describes oxidized lipids for prevention and treatment of atherosclerosis and related diseases.

International Patent Application No. PCT/IL05/000735 (Publication No. WO 06/006161) describes synthetic routes applicable for industrial preparation of therapeutically beneficial oxidized phospholipids without the use of column chromatography.

Additional background art includes International Patent Application Nos. PCT/IL02/00005 (Publication No. WO 02/053092) and PCT/IL08/000,013 (Publication No. WO 08/084,472).

SUMMARY OF THE INVENTION

According to an aspect of some embodiments of the present invention there is provided a compound having the general formula I:

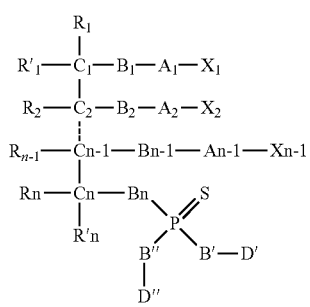

Formula I wherein:

n is an integer of 1-6, whereas if n=1, Cn, Rn and R'n are absent, and $C_1$ is attached to Bn;

each of $B_1, B_2, \ldots Bn-1$ and Bn is independently selected from the group consisting of oxygen, sulfur, nitrogen, phosphorus and silicon, whereby each of the nitrogen, phosphorus and silicon is substituted by at least one substituent selected from the group consisting of hydrogen, lone pair electrons, alkyl, halo, cycloalkyl, aryl, hydroxy, thiohydroxy, alkoxy, aryloxy, thioaryloxy, thioalkoxy and oxo;

each of B' and B" is independently selected from the group consisting of sulfur and oxygen;

each of $A_1, A_2, \ldots An-1$ is independently selected from the group consisting of CR"R'", C=O and C=S;

each of D' and D" is independently selected from the group consisting of hydrogen, alkyl, cycloalkyl, phosphonate and thiophosphonate;

and each of $X_1, X_2, \ldots Xn-1$ is independently a saturated or unsaturated hydrocarbon having the general formula II:

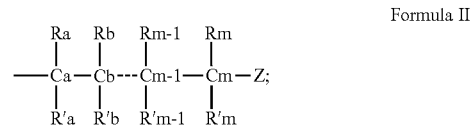

Formula II wherein:

m is an integer of 1-26; and

Z is selected from the group consisting of:

H,

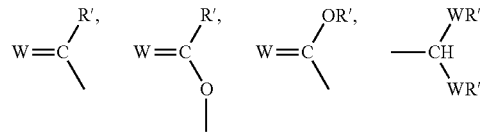

and —OH, whereas:

W is selected from the group consisting of oxygen, sulfur, nitrogen and phosphorus, whereby each of the nitrogen and phosphorus is substituted by at least one substituent selected from the group consisting of hydrogen, lone pair electrons, alkyl, halo, cycloalkyl, aryl, hydroxy, thiohydroxy, alkoxy, aryloxy, thioaryloxy, thioalkoxy and oxo;

R' is selected from the group consisting of hydrogen, alkyl, cycloalkyl, aryl and heteroaryl; and in at least one of $X_1, X_2, \ldots Xn-1$, Z is not hydrogen;

and wherein:

each of $R_1, R'_1, R_2, \ldots Rn-1$, Rn, R'n, each of R" and R'" and each of Ra, R'a, Rb, R'b, ... Rm-1, R'm-1, Rm and R'm is independently selected from the group consisting of hydrogen, a bond, alkyl, alkenyl, alkylnyl, cycloalkyl, aryl, heteroaryl, heteroalicyclic, halo, trihalomethyl, hydroxy, alkoxy, aryloxy, thiohydroxy, thioalkoxy, thioaryloxy, phosphonate, thiophosphonate, phosphate, thiophosphate, phosphinyl, sulfonyl, sulfinyl, sulfonamide, amide, carbonyl, thiocarbonyl, C-carboxy, O-carboxy, O-carbamate, N-carbamate, C-thiocarboxy, S-thiocarboxy and amino, or, alternatively, at least two of $R_1$, R'1, R2, ... Rn-1, Rn and R'n and/or at least two of Ra, R'a, Rb, R'b, ... Rm-1, R'm-1, Rm and R'm form at least one four-, five- or six-membered aromatic, heteroaromatic, alicyclic or heteroalicyclic ring; and each of $C_1, C_2, \ldots, C_{n-1}, C_n$, and each of Ca, Cb, Cm−1 and Cm is a chiral or non-chiral carbon atom, whereby each chiral carbon atom has a S-configuration and/or a R-configuration, or a pharmaceutically acceptable salt, a prodrug, a hydrate or a solvate thereof.

According to an aspect of some embodiments of the present invention there is provided a pharmaceutical composition comprising, as an active ingredient, the compound of general formula I as described herein and a pharmaceutically acceptable carrier.

According to an aspect of some embodiments of the present invention there is provided a method of treating or preventing an inflammation associated with an endogenous oxidized lipid, the method comprising administering to a subject in need thereof a therapeutically effective amount of a compound of general formula I as described herein, thereby treating or preventing the inflammation associated with an endogenous oxidized lipid in the subject.

According to an aspect of some embodiments of the present invention there is provided a method of decreasing a level of a cytokine selected from the group consisting of interleukin-12 and interleukin-23 in a subject, the method comprising administering to the subject an effective amount of a compound of general formula I as described herein.

According to an aspect of some embodiments of the present invention there is provided a method of treating a disease or disorder in which decreasing a level of a cytokine selected from the group consisting of interleukin-12 and interleukin-23 is beneficial, the method comprising administering to a subject in need thereof an effective amount of a compound of general formula I as described herein.

According to an aspect of some embodiments of the present invention there is provided a use of the compound of general formula I as described herein in the manufacture of a medicament for treating or preventing an inflammation associated with an endogenous oxidized lipid.

According to an aspect of some embodiments of the present invention there is provided a use of the compound of general formula I as described herein in the manufacture of a medicament for decreasing a level of a cytokine selected from the group consisting of interleukin-12 and interleukin-23 in a subject.

According to an aspect of some embodiments of the present invention there is provided a use of the compound of general formula I as described herein in the manufacture of a medicament for treating a disease or disorder in which decreasing a level of a cytokine selected from the group consisting of interleukin-12 and interleukin 23 is beneficial.

According to some embodiments, B' and B" are each oxygen.

According to some embodiments, D" is hydrogen.

According to some embodiments, at least one of $A_1, A_2, \ldots$ and An−1 is CR"R'".

According to some embodiments, at least one of the at least one of $A_1, A_2, \ldots$ and An−1 is linked to a $X_1, X_2 \ldots$ or Xn−1 which comprises a Z different than hydrogen.

According to some embodiments, n equals 3.

According to some embodiments, the compound having general formula I has the general formula III:

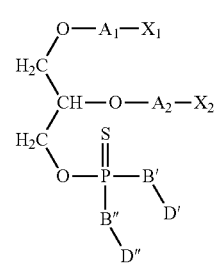

Formula III wherein:
each of $A_1$ and $A_2$ is independently selected from the group consisting of CR"R'", C=O and C=S;
each of B' and B" is independently selected from the group consisting of sulfur and oxygen;
each of D' and D" is independently selected from the group consisting of hydrogen, alkyl, cycloalkyl, phosphonate and thiophosphonate; and
each of $X_1$ and $X_2$ is independently a saturated or unsaturated hydrocarbon having the general formula II:

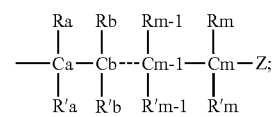

Formula II wherein:
m is an integer of 1-26; and
Z is selected from the group consisting of:
H,

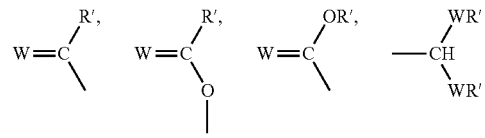

and —OH,
whereas:
W is selected from the group consisting of oxygen, sulfur, nitrogen and phosphorus, whereby each of the nitrogen and phosphorus is substituted by at least one substituent selected from the group consisting of hydrogen, lone pair electrons, alkyl, halo, cycloalkyl, aryl, hydroxy, thiohydroxy, alkoxy, aryloxy, thioaryloxy, thioalkoxy and oxo;
R' is selected from the group consisting of hydrogen, alkyl, cycloalkyl, aryl and heteroaryl; and
in at least one of $X_1$ and $X_2$, Z is not hydrogen;
and wherein:
each of R" and R'" and each of Ra, R'a, Rb, R'b, … Rm−1, R'm−1, Rm and R'm is independently selected from the group consisting of hydrogen, a bond, alkyl, alkenyl, alkylnyl, cycloalkyl, aryl, heteroaryl, heteroalicyclic, halo, trihalomethyl, hydroxy, alkoxy, aryloxy, thiohydroxy, thioalkoxy, thioaryloxy, phosphonate, thiophosphonate, phosphate, thiophosphate, phosphinyl, sulfonyl, sulfinyl, sulfonamide, amide, carbonyl, thiocarbonyl, C-carboxy, O-carboxy, O-carbamate, N-carbamate, C-thiocarboxy, S-thiocarboxy and amino, or, alternatively, at least two of $R_1, R'_1, R_2, \ldots R_{n-1}$, Rn and R'n and/or at least two of Ra, R'a, Rb, R'b, … Rm−1, R'm−1, Rm and R'm form at least one four-, five- or six-membered aromatic, heteroaromatic, alicyclic or heteroalicyclic ring, or a pharmaceutically acceptable salt, a prodrug, a hydrate or a solvate thereof.

According to some embodiments, at least one of $A_1$ and $A_2$ is CR"R'".

According to some embodiments, $A_2$ is CR"R'".

According to some embodiments, each of $A_1$ and $A_2$ is CR"R'".

According to some embodiments, $X_2$ comprises a Z different than hydrogen.

According to some embodiments, the Z that is different than hydrogen is selected from the group consisting of

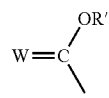

and

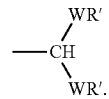

According to some embodiments, W is oxygen and each of R" and R'" is independently selected from the group consisting of hydrogen and alkyl.

According to some embodiments, B' and B" are each oxygen; D" is hydrogen; D' is selected from the group consisting of 2-aminoethyl and N,N,N-trimethyl-2-aminoethyl; and each of $X_1$ and $X_2$ is a saturated hydrocarbon having the general formula II:

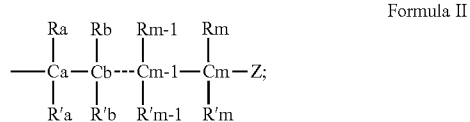

Formula II wherein:
m is an integer of 3-15; and
Z is selected from the group consisting of:
H and

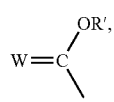

whereas:
W is oxygen; and
in at least one of $X_1$ and $X_2$, Z is not hydrogen; and
each of R', Ra, R'a, Rb, R'b, . . . Rm−1, R'm−1, Rm and R'm is hydrogen.

According to some embodiments, the compound having general formula I has a structure as presented in formula IV:

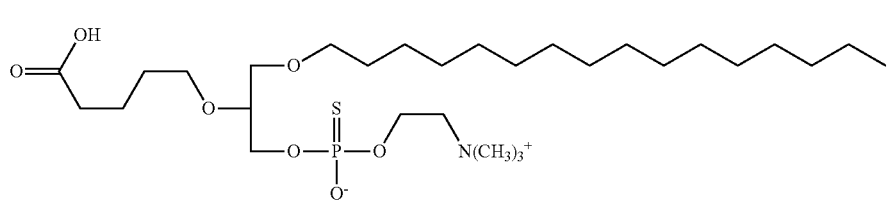

Formula IV or is a pharmaceutically acceptable salt thereof.

According to some embodiments, the compound having general formula I has a structure as presented in formula V:

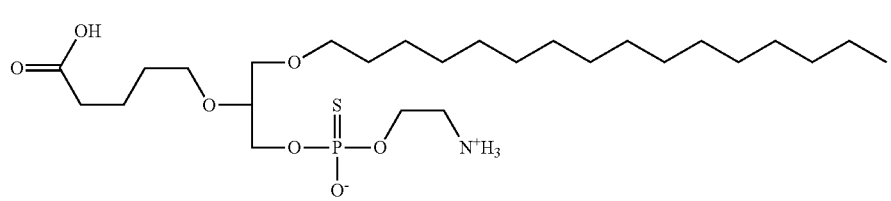

Formula V or is a pharmaceutically acceptable salt thereof.

According to some embodiments, the compound of general formula I is 1-hexadecyl-2-(4-carboxy)butyl-sn-glycero-3-thiophosphorylcholine, or a pharmaceutically acceptable salt thereof.

According to some embodiments, the compound of general formula I is 1-hexadecyl-2-(4-carboxy)butyl-sn-glycero-3-O-thiophosphorylethanolamine, or a pharmaceutically acceptable salt thereof.

According to some embodiments, the pharmaceutical composition described herein is packaged in a packaging material and identified in print, in or on the packaging material, for use in the treatment or prevention of an inflammation associated with an endogenous oxidized lipid.

According to some embodiments, the pharmaceutical composition described herein is packaged in a packaging material and identified in print, in or on the packaging material, for decreasing of a level of a cytokine selected from the group consisting of interleukin-12 and interleukin-23.

According to some embodiments, the pharmaceutical composition described herein is packaged in a packaging material and identified in print, in or on the packaging material, for use in the treatment of a disease or disorder in which decreasing of a level of a cytokine selected from the group consisting of interleukin-12 and interleukin-23 is beneficial.

According to some embodiments, the inflammation is associated with a disease or disorder selected from the group consisting of an idiopathic inflammatory disease or disorder, a chronic inflammatory disease or disorder, an acute inflammatory disease or disorder, an autoimmune disease or disorder, an infectious disease or disorder, an inflammatory malignant disease or disorder, an inflammatory transplantation-related disease or disorder, an inflammatory degenerative disease or disorder, a disease or disorder associated with a hypersensitivity, an inflammatory cardiovascular disease or disorder, an inflammatory cerebrovascular disease or disorder, a peripheral vascular disease or disorder, an inflammatory glandular disease or disorder, an inflammatory gastrointestinal disease or disorder, an inflammatory cutaneous disease or disorder, an inflammatory hepatic disease or disorder, an inflammatory neurological disease or disorder, an inflammatory musculo-skeletal disease or disorder, an inflammatory renal disease or disorder, an inflammatory reproductive disease or disorder, an inflammatory systemic disease or disorder, an inflammatory connective tissue disease or disorder, an inflammatory tumor, necrosis, an inflammatory implant-related disease or disorder, an inflammatory aging process, an immunodeficiency disease or disorder and an inflammatory pulmonary disease or disorder.

According to an aspect of some embodiments of the present invention there is provided a method of introducing a thiophosphate moiety into a compound so as to produce the compound of general formula I described hereinabove, the method comprising:

reacting a thiophosphorus-containing compound having a second reactive group and a third reactive group with a compound having the general formula VI:

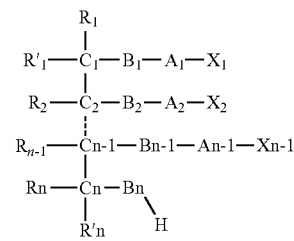

Formula VI wherein:
n is an integer of 1-6, whereas if n=1, Cn, Rn and R'n are absent, and $C_1$ is attached to Bn;

each of $B_1, B_2, \ldots Bn-1$ and Bn is independently selected from the group consisting of oxygen, sulfur, nitrogen, phosphorus and silicon, whereby each of the nitrogen, phosphorus and silicon is substituted by at least one substituent selected from the group consisting of hydrogen, lone pair electrons, alkyl, halo, cycloalkyl, aryl, hydroxy, thiohydroxy, alkoxy, aryloxy, thioaryloxy, thioalkoxy and oxo;

each of $A_1, A_2, \ldots An-1$ is independently selected from the group consisting of CR"R''', C=O and C=S; and each of $X_1, X_2, \ldots Xn-1$ is independently a saturated or unsaturated hydrocarbon having the general formula II:

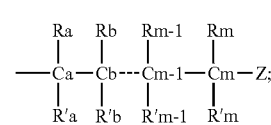

Formula II wherein:
m is an integer of 1-26; and
Z is selected from the group consisting of:
H,

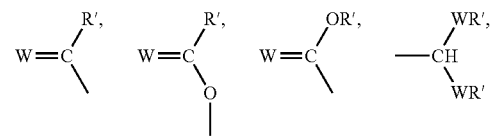

—OH and a pre-oxidized moiety,
whereas:
W is selected from the group consisting of oxygen, sulfur, nitrogen and phosphorus, whereby each of the nitrogen and phosphorus is substituted by at least one substituent selected from the group consisting of hydrogen, lone pair electrons, alkyl, halo, cycloalkyl, aryl, hydroxy, thiohydroxy, alkoxy, aryloxy, thioaryloxy, thioalkoxy and oxo;

R' is selected from the group consisting of hydrogen, alkyl, cycloalkyl, aryl and heteroaryl; and in at least one of $X_1, X_2, \ldots Xn-1$, Z is not hydrogen;

and wherein:
each of $R_1, R'_1, R_2, \ldots Rn-1, Rn, R'n$, each of R" and R''' and each of Ra, R'a, Rb, R'b, ... Rm-1, R'm-1, Rm and R'm is independently selected from the group consisting of hydrogen, a bond, alkyl, alkenyl, alkylnyl, cycloalkyl, aryl, heteroaryl, heteroalicyclic, halo, trihalomethyl, hydroxy, alkoxy, aryloxy, thiohydroxy, thioalkoxy, thioaryloxy, phosphonate, thiophosphonate, phosphate, thiophosphate, phosphinyl, sulfonyl, sulfinyl, sulfonamide, amide, carbonyl, thiocarbonyl, C-carboxy, O-carboxy, O-carbamate, N-carbamate, C-thiocarboxy, S-thiocarboxy and amino, or, alternatively, at least two of $R_1$, $R'_1$, $R_2$, ... $Rn-1$, $Rn$ and $R'n$ and/or at least two of $Ra$, $R'a$, $Rb$, $R'b$, ... $Rm-1$, $R'm-1$, $Rm$ and $R'm$ form at least one four-, five- or six-membered aromatic, heteroaromatic, alicyclic or heteroalicyclic ring; and each of $C_1$, $C_2$, ..., $Cn-1$, $Cn$, and each of $Ca$, $Cb$, $Cm-1$ and $Cm$ is a chiral or non-chiral carbon atom, whereby each chiral carbon atom has a S-configuration and/or a R-configuration, or a pharmaceutically acceptable salt, a prodrug, a hydrate or a solvate thereof, the second reactive group being capable of reacting with Bn, to thereby provide a compound having a reactive thiophosphorus-containing group attached to Bn; and converting the reactive thiophosphorus-containing group to the thiophosphate moiety, thereby producing the compound having general formula I described hereinabove, wherein when Z in Formula VI is a pre-oxidized moiety, the method further comprises oxidizing the pre-oxidized moiety. According to some embodiments, Bn is selected from the group consisting of oxygen and sulfur.

According to some embodiments, the pre-oxidized moiety is an unsaturated alkyl (e.g., alkenyl). In some embodiments, the unsaturated alkyl is such that the unsaturated double bond is at a terminus position, and hence is capable of readily undergoing oxidation reaction so as to produce an oxidized moiety.

According to some embodiments, the thiophosphorus-containing compound is $PSCl_3$.

According to some embodiments, the reacting is performed in the presence of a base.

According to some embodiments, the base is a tertiary amine.

According to some embodiments, the reactive thiophosphorus-containing group is a dichlorothiophosphate group.

According to some embodiments, the compound having the general formula VI has a saturated or unsaturated hydrocarbon having the general formula II as described herein attached thereto via an ether bond.

According to some embodiments, the thiophosphate moiety is thiophosphoric acid and the converting comprises hydrolyzing the reactive thiophosphorus-containing group.

According to some embodiments, the thiophosphate moiety comprises an alkylamino group and the converting comprises reacting the reactive thiophosphorus-containing moiety with a derivative of an aminoalkyl, the derivative being capable of reacting with the reactive thiophosphorus-containing group.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying figures. With specific reference now to the figures in detail, it is stressed that the particulars shown are by way of example and for purposes of illustrative discussion of embodiments of the invention. In this regard, the description taken with the figures makes apparent to those skilled in the art how embodiments of the invention may be practiced.

In the drawings.

DESCRIPTION OF SPECIFIC EMBODIMENTS OF THE INVENTION

Figure 1:
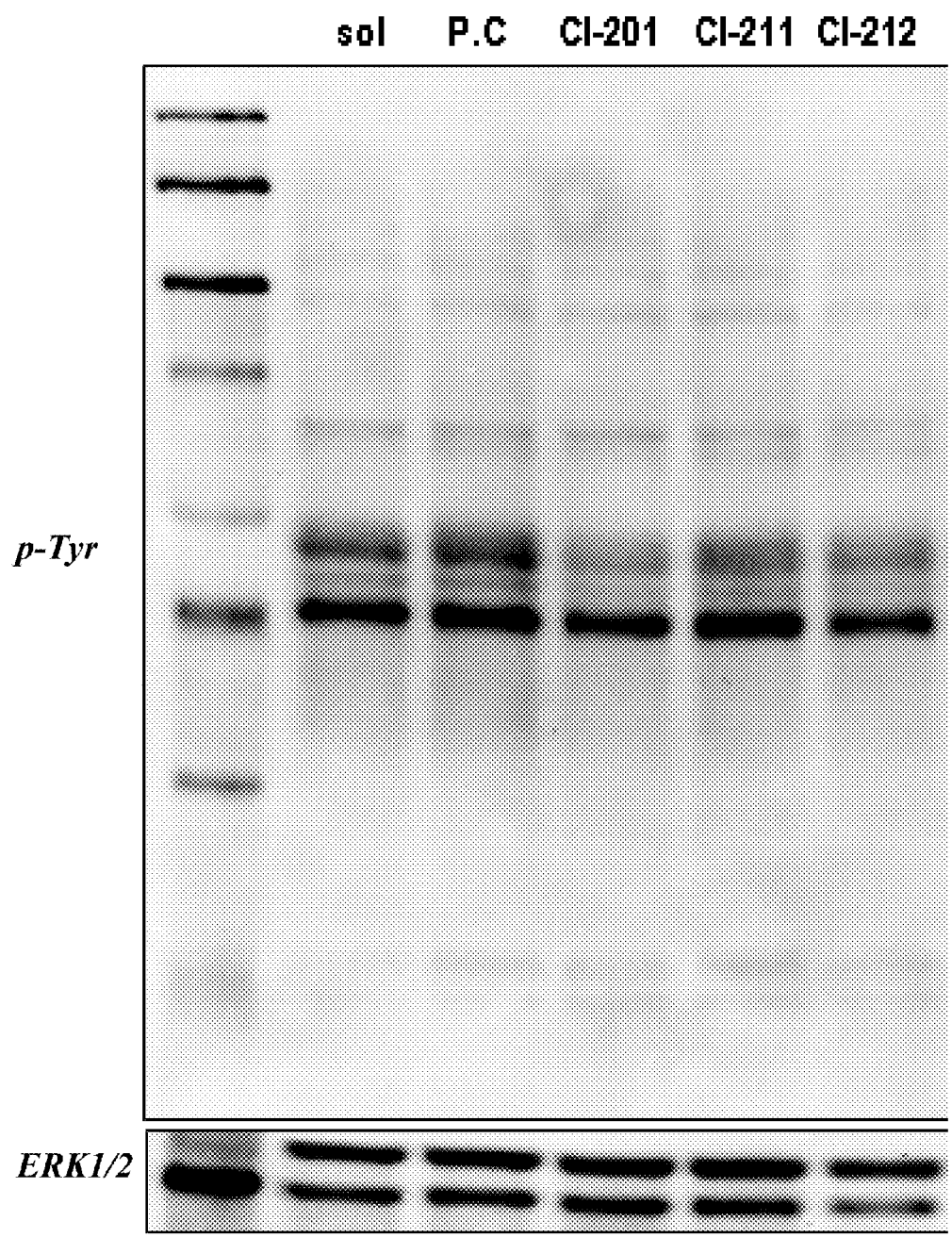
FIG. 1 presents a photograph of a Western blot showing reduction of phosphotyrosine (p-Tyr) by the oxidized thiophospholipids CI-211 and CI-212; phosphatidylcholine (P.C.) and solvent (sol) with no lipid compound served as negative controls, and the oxidized phospholipid CI-201 served as a positive control for reduction of phosphotyrosine; ERK1/2 served as a control for protein loading.

The present invention relates, in some embodiments thereof, to novel oxidized thiophospholipids and to methods employing oxidized thiophospholipids for treating or preventing an inflammation associated with endogenous oxidized lipids. The methods of the present embodiments can be utilized in treating or preventing inflammation-associated diseases and disorders such as, for example, atherosclerosis and related disorders, autoimmune diseases or disorders, and proliferative disease or disorders.

The principles and operation of the present invention may be better understood with reference to the figures and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Experimental and clinical evidence indicates a causative role for oxidized LDL (ox LDL) and LDL components in the etiology of an excessive inflammatory response in atherosclerosis. Both cellular and humoral immune reactivity to plaque related oxidized LDL have been demonstrated, suggesting an important anti-oxidized LDL autoimmune component in atherogenesis. Thus, LDL, oxidized LDL and components thereof, have been the targets of numerous therapies for prevention and treatment of heart disease, cerebral-vascular disease and peripheral vascular disease.

A role of oxidized phospholipids in treating inflammation is disclosed in International Patent Application No. PCT/IL2004/000453 (Publication No. WO 04/106486) and U.S. patent application Ser. No. 11/528,657 (Publication No. 2007-0099868) by the present assignee, both of which are incorporated herein by reference.

In an attempt to improve treatment of inflammation and diseases and disorders associated with oxidized lipids, the present inventors have designed novel synthetic oxidized thiophospholipids and structurally related compounds, which are designed to exhibit improved anti-inflammatory effect and/or improved pharmacological performance in terms of, for example, improved biostability, improved bioavailability and/or reduced toxicity.

Hence, the present inventors have tested the effects of oxidized thiophospholipids, a group of non-natural compounds which are structurally related to oxidized phospholipids present in oxidized LDL, on immune reactivity, and hence as therapeutically active agents for the treatment or prevention of a myriad of diseases and disorders, associated with inflammation and/or altered immune response, such as, for example, atherosclerosis and related diseases or disorders, as well as other diseases and disorder associated with endogenous oxidized lipid.

As is demonstrated in the Examples section that follows, while reducing the present invention to practice, it was indeed confirmed that newly designed oxidized thiophospholipids modulate a cytokine production associated with immune and/or inflammatory response to endogenous oxidized LDL, thereby exhibiting a capability to reduce an inflammatory response in inflammatory diseases such as atherosclerosis and rheumatoid arthritis.

FIG. 1 shows that exemplary oxidized thiophospholipids, according to some embodiments of the invention, exhibit effects on protein phosphorylation similar to those exhibited by the oxidized phospholipid CI-201 (also known as VB-201), a known anti-inflammatory compound.

Figure 2:
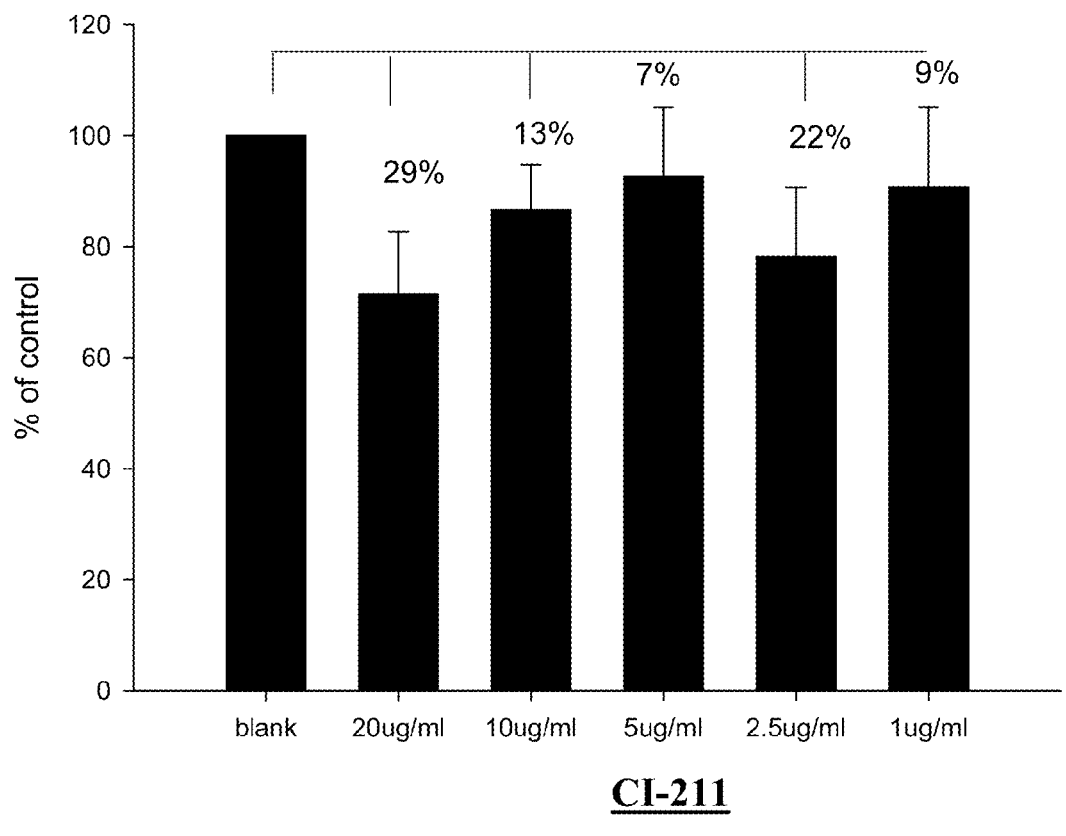
FIG. 2 is a graph showing IL12/23p40 secretion by peptidoglycan-activated BMDCs following treatment with 0 μg/ml (blank), 1 μg/ml, 2.5 μg/ml, 5 μg/ml, 10 μg/ml and 20 μg/ml of CI-211.

FIG. 2 shows inhibition by an exemplary oxidized thiophospholipid, according to some embodiments of the invention, of in vitro production of the p40 subunit of the pro-inflammatory cytokines interleukin-12 and interleukin-23.

The performance of the oxidized thiophospholipids described herein can be further tested in vivo, in suitable animal models such as, for example, those described in International Patent Application No. PCT/IL2004/000453 (Publication No. WO 04/106486) and U.S. patent application Ser. No. 11/528,657 (Publication No. 2007-0099868), and in models designed as described in Singh et al., Clinical Chemistry 51:12, 2252-2256 (2005), which is incorporated by reference as if fully set forth herein.

The improved biostability of the oxidized thiophospholipids can be determined, for example, by assaying its enzymatic degradation by phospholipase-C, using ELISA or absorbance measurements. Phospholipase-C is known to catalyze degradation of oxidized phospholipids, but its effect on corresponding synthetic thiophospholipids has not been determined hitherto.

The improved bioavailability of the oxidized thiophospholipds described herein can be determined in in vivo animal models known in the art.

The toxicity of the oxidized thiophospholipids described herein can also readily be determined by measuring $LD_{50}$ values and toxicity indexes of the compounds, as is well known in the art.

The oxidized thiophospholipids described herein cam therefore be advantageously recognized as exhibiting an improved effect in treating or preventing inflammation associated with endogenous oxidized lipids, in terms of improved therapeutic and/or pharmacokinetic parameters.

Thus, according to an aspect of some embodiments of the present invention there are provided novel compounds, designed so as to mimic the immunomodulation effect induced by oxidized LDL and/or an inflammation associated with oxidized LDL and/or other oxidized lipids, and which are thus highly suitable for treatment of inflammatory associated diseases and disorders which involve oxidized lipids.

The compounds described herein can be collectively represented by the general formula I:

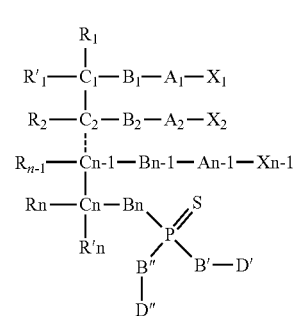

Formula I wherein:

n is an integer of 1-6, whereas if n=1, Cn, Rn and R'n are absent, and $C_1$ is attached to Bn;

each of $B_1, B_2, \ldots Bn-1$ and Bn is independently selected from the group consisting of oxygen, sulfur, nitrogen, phosphorus and silicon, whereby each of the nitrogen, phosphorus and silicon is substituted by at least one substituent selected from the group consisting of hydrogen, lone pair electrons, alkyl, halo, cycloalkyl, aryl, hydroxy, thiohydroxy, alkoxy, aryloxy, thioaryloxy, thioalkoxy and oxo;

each of B' and B" is independently selected from the group consisting of sulfur and oxygen (e.g., oxygen);

each of $A_1, A_2, \ldots An-1$ is independently selected from the group consisting of CR"R'", C=O and C=S;

each of D' and D" is independently selected from the group consisting of hydrogen, alkyl, cycloalkyl, phosphonate and thiophosphonate; and each of $X_1, X_2, \ldots Xn-1$ is independently a saturated or unsaturated hydrocarbon having the general formula II:

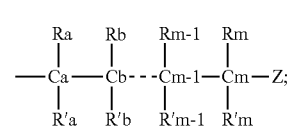

Formula II wherein:

m is an integer of 1-26; and

Z is selected from the group consisting of:

H,

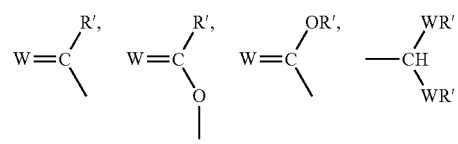

and —OH, whereas:

W is selected from the group consisting of oxygen, sulfur, nitrogen and phosphorus, whereby each of the nitrogen and phosphorus is substituted by at least one substituent selected from the group consisting of hydrogen, lone pair electrons, alkyl, halo, cycloalkyl, aryl, hydroxy, thiohydroxy, alkoxy, aryloxy, thioaryloxy, thioalkoxy and oxo;

R' is selected from the group consisting of hydrogen, alkyl, cycloalkyl, aryl and heteroaryl; and in at least one of $X_1, X_2, \ldots Xn-1$, Z is not hydrogen; and wherein:

each of $R_1$, $R'_1$, $R_2$, ... $R_{n-1}$, $R_n$, $R'_n$, each of R" and R'" and each of Ra, R'a, Rb, R'b, ... $R_{m-1}$, $R'_{m-1}$, Rm and R'm is independently selected from the group consisting of hydrogen, a bond, alkyl, alkenyl, alkylnyl, cycloalkyl, aryl, heteroaryl, heteroalicyclic, halo, trihalomethyl, hydroxy, alkoxy, aryloxy, thiohydroxy, thioalkoxy, thioaryloxy, phosphonate, thiophosphonate, phosphate, thiophosphate, phosphinyl, sulfonyl, sulfinyl, sulfonamide, amide, carbonyl, thiocarbonyl, C-carboxy, O-carboxy, O-carbamate, N-carbamate, C-thiocarboxy, S-thiocarboxy and amino, or, alternatively, at least two of $R_1$, $R'_1$, R2, ... $R_{n-1}$, Rn and R'n and/or at least two of Ra, R'a, Rb, R'b, ... $R_{m-1}$, $R'_{m-1}$, Rm and R'm form at least one four-, five- or six-membered aromatic, heteroaromatic, alicyclic or heteroalicyclic ring, or a pharmaceutically acceptable salt, a prodrug, a hydrate or a solvate thereof.

It will be appreciated by one of ordinary skill in the art that the feasibility of each of the substituents (e.g., $R_1$—Rn, Ra-Rm, R", R'") to be located at the indicated positions depends on the valency and chemical compatibility of the substituent, the substituted position and other substituents. Hence, the compounds of embodiments of the present invention are aimed at encompassing all the feasible substituents for any position.

As used herein throughout, the term "alkyl" refers to a saturated or unsaturated aliphatic hydrocarbon including straight chain and branched chain groups. In some embodiments, the alkyl is saturated except where specifically stated otherwise. Optionally, the alkyl group has 1 to 30 carbon atoms, optionally 1-20. Whenever a numerical range; e.g., "1-30", is stated herein, it implies that the group, in this case the alkyl group, may contain 1 carbon atom, 2 carbon atoms, 3 carbon atoms, etc., up to and including 30 carbon atoms. Optionally, the alkyl is a medium size alkyl having 1 to 10 carbon atoms. Optionally, the alkyl is a lower alkyl having 1 to 4 carbon atoms, unless otherwise indicated. The alkyl group may be substituted or unsubstituted. When substituted, the substituent group can be, for example, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, 0-thiocarbamyl, N-thiocarbamyl, C-amido, N-amido, C-carboxy, O-carboxy, sulfonamido, and amino, as these terms are defined herein.

An "alkenyl" group refers to an unsaturated alkyl group which consists of at least two carbon atoms and at least one carbon-carbon double bond.

An "alkynyl" group refers to an unsaturated alkyl group which consists of at least two carbon atoms and at least one carbon-carbon triple bond.

As used herein, the term "hydrocarbon" refers to a compound that includes hydrogen atoms and carbon atoms, covalently attached therebetween. This term encompasses alkyls, alkenyls, cycloalkyls and aryls, and any combination thereof, as defined herein.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. Optionally, the aryl is unsubstituted or comprises a single substituent. In some embodiments, the aryl is unsubstituted, except when indicated otherwise. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein. Representative examples are piperidine, piperazine, tetrahydrofuran, tetrahydropyran, morpholine and the like.

As used herein, the term "thiophospholipid" refers to a lipid or structural analog thereof which comprises a thiophosphate group and/or thiophosphonate group. The term encompasses any natural or synthetically prepared compound that has common structural features with a natural lipid, an oxidized lipid, and any components, moieties, analogs and derivatives thereof, along with a thiophosphate group and/or thiophosphonate group. Optionally, the oxidized thiophospholipid is a derivative of a natural oxidized lipid (e.g., an oxidized phospholipid), or any component (e.g., a component of LDL), moiety or derivative (e.g., etherified derivative)

thereof, wherein a phosphate or phosphonate group is replaced by a thiophosphate or thiophosphonate group.

As used herein, the terms "thiophosphate" and "thiophosphoryl" refer to a —Y'"—P(=Y")(—YR)—Y'—R group or to a —Y'"—P(=Y")(—YR)—Y'— group, wherein each of Y, Y', Y" and Y'" is independently oxygen or sulfur, provided that at least one of Y, Y' and Y" is sulfur, and wherein R is independently hydrogen, alkyl, alkenyl, cycloalkyl, aryl, heteroaryl (bonded through a ring carbon) or heteroalicyclic (bonded through a ring carbon) as defined herein. In some embodiments, at least Y" is sulfur.

As used herein, the terms "thiophosphonate" and "thiophosphonyl" refer to a —P(=Y")(—YR)—Y'—R group or to a —P(=Y")(—YR)—Y'— group, wherein each of Y, Y' and Y" is independently oxygen or sulfur, provided that at least one of Y, Y' and Y" is sulfur, and wherein R is as defined herein. In some embodiments, at least Y" is sulfur.

A "hydroxy" group refers to an —OH group.

An "azide" group refers to a —N=N=N group.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" group refers to a —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "carbonyl" group refers to a —C(=O)—R group, where R is hydrogen, alkyl, alkenyl, cycloalkyl, aryl, heteroaryl (bonded through a ring carbon) or heteroalicyclic (bonded through a ring carbon) as defined herein.

An "aldehyde" group refers to a carbonyl group, where R is hydrogen.

A "thiocarbonyl" group refers to a —C(=S)—R group, where R is as defined herein.

A "C-carboxy" group refers to a C(=O)—O—R groups, where R is as defined herein.

An "O-carboxy" group refers to an RC(=O)—O— group, where R is as defined herein.

A "C-thiocarboxy" group refers to C(=S)—O—R and —C(=O)—SR groups, where R is as defined herein.

An "S-thiocarboxy" group refers to an RC(=O)—S— group, where R is as defined herein.

An "oxo" group refers to a =O group.

A "carboxylic acid" group refers to a C-carboxyl group in which R is hydrogen.

A "halo" group refers to fluorine, chlorine, bromine or iodine.

A "trihalomethyl" group refers to a —CX$_3$ group wherein X is a halo group as defined herein.

A "sulfinyl" group refers to an —S(=O)—R group, where R is as defined herein.

A "sulfonyl" group refers to an —S(=O)$_2$—R group, where R is as defined herein.

A "sulfonamide" or "sulfonamido" group encompasses S-sulfonamido and N-sulfonamide groups, as defined herein.

An "S-sulfonamido" group refers to a S(=O)$_2$—NR$_2$ group, with each R as defined herein.

An "N-sulfonamido" group refers to an RS(=O)$_2$—NR— group, where each R is as defined herein.

An "O-carbamate" or "O-carbamyl" group refers to an —OC(=O)—NR$_2$ group, where each of R and R' as defined herein.

An "N-carbamate" or "N-carbamyl" group refers to an ROC(=O)—NR— group, where each R is as defined herein.

An "O-thiocarbamyl" group refers to an —OC(=S)—NR$_2$ group, where each R is as defined herein.

An "N-thiocarbamyl" group refers to an ROC(=S)NR— group, where each R is as defined herein.

An "amino" group refers to an —NR$_2$ group where each R is as defined herein.

An "amide" or "amido" group encompasses "C-amido" and "N-amido" groups, as defined herein.

A "C-amido" group refers to a —C(=O)—NR$_2$ group, where each R is as defined herein.

An "N-amido" group refers to an RC(=O)—NR— group, where each R is as defined herein.

An "urea" group refers to an —NRC(=O)—NR$_2$ group, where each R is as defined herein.

A "nitro" group refers to an —NO$_2$ group.

A "cyano" group refers to a —C≡N group.

The term "phosphonyl" or "phosphonate" describes a —P(=O)(OR)$_2$ group, with each R as defined hereinabove.

The term "phosphate" or "phosphoryl" describes an —O—P(=O)(OR)$_2$ group, with each R as defined hereinabove.

A "phosphoric acid" is a phosphate group is which each R is hydrogen.

The term "phosphinyl" describes a —PR$_2$ group, with each R is as defined hereinabove.

The term "thiourea" describes a —NR—C(=S)—NR— group, with each R is as defined hereinabove.

The term "saccharide" refers to one or more sugar unit, either an open-chain sugar unit or a cyclic sugar unit (e.g., pyranose- or furanose-based units), and encompasses any monosaccharide, disaccharide and oligosaccharide, unless otherwise indicated.

As is shown in the general formula I above, the compounds as described herein include a backbone of 1-6 carbon atoms, preferably 2-6 carbon atoms (e.g., wherein n in formula I is 2-6), whereby at least one of these backbone carbon atoms is covalently attached to a thiophosphate moiety, as defined herein, and the other 1-5 backbone carbon atoms are covalently attached to hydrocarbon chains ($X_1$-$X_n$–1) via a heteroatom ($B_1$-$B_{n-1}$ in the general formula I above), or, when n=1, the single backbone carbon atom is attached to both a thiophosphate moiety and a hydrocarbon chain. These hydrocarbon chains can include saturated or unsaturated, substituted or unsubstituted chains, optionally interrupted by aromatic, alicyclic, heteroalicyclic and/or heteroaromatic moieties, all as described hereinabove and depicted in general formula II, whereby at least one of these chains is terminating with an oxidized group, defined hereinabove as Z that is different than hydrogen.

Each of the hydrocarbon chains according to the present embodiments can include between 1 and 26 carbon atoms, optionally between 3 and 26 carbon atoms. Hydrocarbon chains that terminate with the oxidized group Z are typically lower-sized chains, optionally having between 3 and 10 carbon atoms, and optionally between 3 and 6 carbon atoms, not including the carbon atom in the oxidized group.

When the hydrocarbon chain is saturated, each of Ca-Cm is covalently attached to its neighboring atoms via a single sigma bond. When the hydrocarbon is unsaturated, at least two neighboring atoms of Ca-Cm are attached therebetween via a double bond or a triple bond.

In general formula I, D' and D" are independently hydrogen or substituents of the thiophosphate moiety, which may be, as non-limiting example, alkyl, cycloalkyl, phosphonate or thiophosphonate.

Alkyl (e.g., amino-substituted alkyl) and cycloalkyl substituents may be considered as moieties derived from an alcohol attached to the thiophosphate group. Thus, for example, a substituent D' or D" which is 2-aminoethyl may be described as being derived from an amino alcohol (e.g., ethanolamine). Additional amino alcohols which are optionally attached to the thiophosphate group include, for example, choline, serine, ethanolamine-N-lactose, and ethanolamine-N—[methoxy(propylene glycol)]. Additional alcohols which are optionally attached to the thiophosphate group include, for example, methanol, ethanol, propanol, butanol, inositol, inositol-4-phosphate, inositol-4,5-diphosphate and glycerol.

Optionally, D' or D" is a substituted alkyl (e.g., substituted glycerol) which is substituted by a phospholipid or thiophospholipid moiety. Thus, for example, the thiophospholipid may be two moieties having the general formula I which are linked by a single D' group. Such compounds may be structurally analogous to cardiolipins.

Phosphonate and thiophosphonate substituents of the thiophosphate group form a sulfur-containing derivative of pyrophosphate.

According to exemplary embodiments, D" is hydrogen.

It is to be understood that for embodiments in which a phosphorus atom is attached by a double bond to a sulfur atom and by a single bond to hydroxy (e.g., —P(=S)(—OH)—), compounds with a phosphorus atom attached by a double bond to an oxygen atom and by a single bond to thiohydroxy (e.g., —P(=O)(—SH)—) are also intended.

LDL is a lipoprotein composed of functionally different moieties (components). Among these moieties are phospholipids, which are considered to play an important role in the effect of oxidized LDL on plaque related diseases.

As used herein throughout, the term "moiety" or "component" refers to a major portion of a functional molecule which is linked to another molecule, while retaining its activity. Phospholipids are natural substances that include a non-polar lipid group and a highly polar phosphoryl group at the end. The most prevalent phospholipids in nature are phosphoglycerides, which include a glycerol backbone and fatty acyl moieties attached thereto. Phosphoglycerides such as 1,2-O-fatty acyl phosphoglycerides, as well as oxidative modifications thereof such as POVPC and PGPC, have been involved in atherogenesis related studies, as is described in detail hereinabove.

In addition to LDL, phospholipids and phosphoglycerides, other lipids are involved in various biological processes such as inflammation. These include, for example, sphingolipids, glycolipids and other membrane lipids.

According to optional embodiments of the present invention, the oxidized thiophospholipid is an analog of a phosphoglyceride, such that in an exemplary embodiment of the present invention n in the general formula I above equals 3.

As used herein throughout, the term "analog" refers to compounds that are structurally related to the subject molecule (e.g., oxidized phospholipids, oxidized phosphoglycerides, etc.) and can therefore exert the same biological activity.

The term "derivatives" refers to subject molecules which has been chemically modified but retain a major portion thereof unchanged, e.g., subject molecules which are substituted by additional or different substituents, subject molecules in which a portion thereof has been oxidized or hydrolysed, and the like.

According to optional embodiments, the compound having general formula I wherein n=3 is a compound having the general formula III:

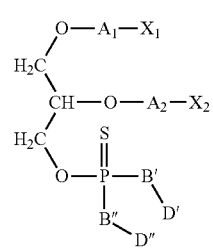

Formula III wherein:
each of $A_1$ and $A_2$ is independently selected from the group consisting of CR"R'", C=O and C=S, whereas R" and R'" are as defined herein for general formula I;

each of B' and B" is independently selected from the group consisting of sulfur and oxygen;

each of D' and D" is independently selected from the group consisting of hydrogen, alkyl, cycloalkyl, phosphonate and thiophosphonate; and each of $X_1$ and $X_2$ is independently a saturated or unsaturated hydrocarbon having the general formula II described hereinabove, or a pharmaceutically acceptable salt, a prodrug, a hydrate or a solvate thereof.

Compounds having Formula III above, in which the carbon atoms that form the glycerolic backbone are substituted by one or more substituents other than hydrogen (as described, for example, for $R_1$, $R'_1$, $R_2$, ... $Rn-1$, $Rn$, $R'n$ in general Formula I hereinabove, are also contemplated.

In view of the inherent instability of the O-fatty acyl moiety in certain naturally occurring phospholipids (e.g., phosphoglycerides), as well as in other structurally related compounds, which results from its high susceptibility to fast hydrolysis in biological systems by phospholipase $A_2$ (see, for example, "A Textbook of Drug Design and Development", Povl Krogsgaard-Larsen and Hans Bundgaard, eds., Harwood Academic Publishers, chapter 13, pages 478-480), the compounds described herein have been designed in some embodiments of the present invention to include at least one fatty ether moiety, i.e., in the general formula I above, at least one of $A_1$, $A_2$, ... and An–1 is a CR"R'" group. Compounds in which one of $A_1$, $A_2$, to An–1 is a CR"R'" group are referred to herein as etherified. Thus, for example, compounds wherein n is 3 and one of $A_1$ and $A_2$ is CR"R'" are referred to herein as mono-etherified phosphoglyceride analogs, while compounds wherein n is 3 and both $A_1$ and $A_2$ are CR"R'" are referred to herein as di-etherified phosphoglyceride analogs. Etherified compounds are characterized by improved in vivo stability, particularly as compared with the presently known oxidized phosphoglycerides (e.g., POVPC and PGPC).

Without being bound by any particular theory, it is believed that improved resistance to hydrolysis is particularly useful for an oxidized side chain of the oxidized thiophospholipid, as the oxidized side chain is believed to play an important role in the biological effects of oxidized thiophospholipid.

Hence, according to some embodiments, at least one of the abovementioned $A_1$, $A_2$, ... and An–1 which is CR"R'", is linked to a to a $X_1$, $X_2$ ... or Xn–1 which comprises a Z which is different than hydrogen (e.g., the $X_1$, $X_2$ ... or Xn–1 is oxidized).

In exemplary embodiments wherein n is 3, $A_2$ is CR"R'". In some embodiments, each of $A_1$ and $A_2$ is CR"R'".

According to some embodiments, n is 3, and $X_2$ comprises a Z different than hydrogen. As discussed herein, when $X_2$ comprises a Z different than hydrogen, $A_2$ is optionally CR"R'". In some embodiments, a Z which is different than hydrogen is

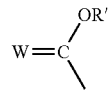

or

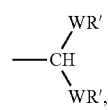

wherein W is as defined herein (e.g., oxygen) and the R' groups are as defined herein (e.g., independently hydrogen or alkyl).

Because in naturally occurring oxidized LDL derivatives the oxidized alkyl chain is typically located at the second position, and since it has been demonstrated that the biological activity of several phospholipids directly depends on the structure thereof (see International Patent Application No. PCT/IL2004/000453 (Publication No. WO 04/106486) for a detailed discussion), it is believed that oxidized thiophospholipids in which $X_2$ comprises a Z different than hydrogen are particularly suitable for mimicking the biological effects of oxidized LDL derivatives.

According to exemplary embodiments, B' and B" are each oxygen; D" is hydrogen; D' is 2-aminoethyl or N,N,N-trimethyl-2-aminoethyl; and each of $X_1$ and $X_2$ is a saturated hydrocarbon having the general formula II:

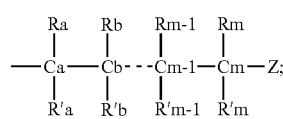

Formula II wherein:
m is an integer of 3-15; and Z is selected from the group consisting of H and

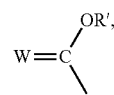

whereas W is oxygen; and in at least one of $X_1$ and $X_2$, Z is not hydrogen; and each of R', Ra, R'a, Rb, R'b, . . . Rm-1, R'm-1, Rm and R'm is hydrogen.

Exemplary compounds include 1-hexadecyl-2-(4-carboxy)butyl-sn-glycero-3-thiophosphorylcholine (also referred to herein as CI-211), wherein D' is N,N,N-trimethyl-2-aminoethyl, and 1-hexadecyl 2 (4 carboxy)butyl-sn-glycero-3-β-thiophosphorylethanolamine (also referred to herein as CI-212), in which D' is 2-aminoethyl.

These compounds are structurally presented as follows:

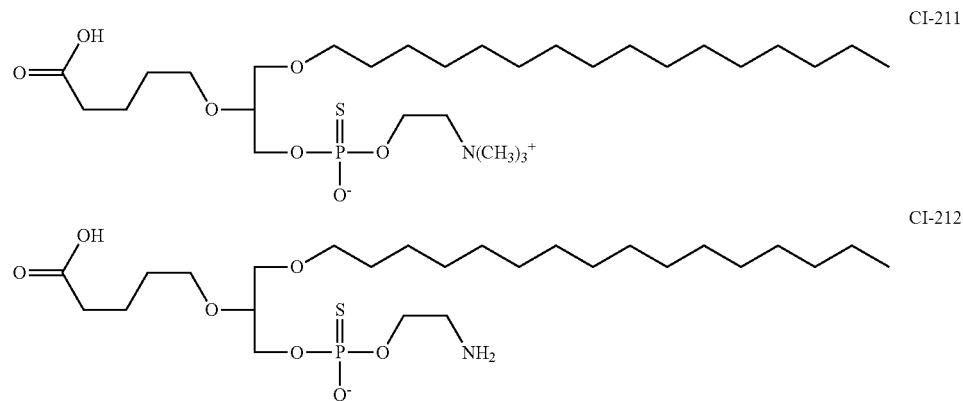

The above compounds comprise a chiral carbon center ($C_2$ of the backbone) and may optionally be R-enantiomers, S-enantiomers or racemates.

The stereochemistry of the compound may be determined, for example, by using a chiral starting material, and reaction conditions which preserve chirality (e.g., by preserving the chiral configuration of the starting material to obtain a product with the chirality of the starting material, or by reversing the chirality of the starting material to obtain a product with an opposite chirality to that of the starting material).

Thus, as exemplified hereinbelow, the chiral starting material (R)-(−)-2,2-dimethyl-1,3-dioxolane-4-methanol (a derivative of glycerol) is used to obtain thiophospholipids with a chiral glycerolic backbone.

While the oxidized thiophospholipids described above are derived from phosphoglycerides, oxidized thiophospholipids derived from, for example, sphingolipids (e.g., sphingomyelin), are also within the scope of the present embodiments. Some oxidized sphingolipid analogs according to the present embodiments have the general formula I above, wherein n equals 3, $B_2$ is NH, and $A_2$ is C=O, whereby the hydrocarbon chain terminating with an oxidized group is attached either to the amide, as $X_2$ or to $C_1$. In addition, some sphingolipid analogs have the general formula I, wherein n equals 2, $B_1$ is NH, $A_1$ is C=O, and at least one of $R_1$ and $R'_1$ is alkyl.

While oxidized thiophospholipid analogs of phosphoglycerides are optionally derived from glycerol, which is a monosaccharide molecule, and oxidized thiophospholipid analogs of sphingolipids are optionally derived from sphingosine, an amino alcohol, it is envisioned that oxidized thiophospholipids derived from other biologically prevalent alcohol base units would exert the same effect. Furthermore, since no correlation between the distance of the oxidized moiety and the phosphate or thiophosphate moieties in oxidized lipids has been established, it is envisioned that oxidized thiophospholipids that are derived from a 4-6 carbon atom backbone would retain structure characteristics similar to those of oxidized thiophospholipid analogs of oxidized phosphoglycerides and as such in all probability would possess the same antigenicity and immune modulation activity, and employed and applied similarly to the oxidized phosphoglyceride analogs described herein.

Optionally, such an alcohol base unit is a monosaccharide base unit, such as, for example, glucose, erythritol and threitol.

Thus, in another optional embodiment, the compounds as described herein include up to 6 carbon atoms (e.g., 5 or 6) in the backbone chain. The carbon atoms in the backbone chain can be linearly attached one to another, so as to form an open-chain monosaccharide backbone, or alternatively, can form a heteroalicyclic monosaccharide backbone, namely a pyranose or furanose backbone, such that in the general formula I above, one of $R_1$ and $R'_1$ is covalently attached to one of Rn or R'n via an etheric bond (an R—O—R bond)

Still alternatively, the compounds as described herein can include 4-6 carbon atoms in the backbone chain, which form a non-saccharidic ring, namely a four-, five- or six-membered carbocyclic or heteroalicyclic ring, such that in the general formula I above one of $R_1$ and $R'_1$ is covalently attached to one of Rn or R'n, via different bonds (e.g., a sigma bond, a π bond, a carboxylic bond, an ether bond, a thioether bond and any other bond).

Although naturally occurring phospholipids and oxidized phospholipids typically include hydrocarbon side chains attached to the backbone by a carboxy group (e.g., via an ester bond), there is evidence that thiocarboxy and thioalkoxy derivatives of may exert the same biological activity (see, for example, Reddy et al. Antitumor ether lipids: an improved synthesis of ilmofosine and an enantioselective synthesis of an ilmofosine analog. Tetrahedron Letters. 1994; 17:2679-2682; Batia and Hajdu. Stereospecific synthesis of ether and thioether phospholipids. The use of L-glyceric acid as a chiral phospholipids precursor. J. Org. Chem. 1988; 53:5034-5039; Bosies et al. Lipids. 1987; 22:947; Bosies et al. Ger. Offen. DE 3,906,952 [C.A. 1991, 114, 102394w]; and Herrmann et al. NCI-EORTC Symposium on New Drugs in Cancer Therapy, Amsterdam, March 1992). Such thio derivatives are often characterized by enhanced biostability, hence such compounds can further be highly beneficial.

Hence, in one embodiment of the present invention, at least one of $B_1$-Bn is sulfur, such that at least one of the side chains is attached to the backbone via a thiocarboxy group (wherein the adjacent A is C═O or C═S) or a thioalkoxy group (wherein the adjacent A is CR"R'"). In another embodiment, at least one of $X_1$-Xn−1 which comprises an oxidized group is linked to such a thiolated side chain.

Alternatively, each of $B_1$-Bn can be a biocompatible heteroatom other than oxygen and sulfur, such as, for example, nitrogen, phosphorus or silicon, as is described within the general formula I hereinabove.

Apart from the structural features delineated herein, the compounds as described herein can be further substituted at any position thereof, e.g., at any of the side chain carbon atoms and at any of the backbone carbon atoms. While a myriad of possible substituents delineated hereinabove and encompassed by the present embodiments, preferred substituents include, for example, halo and aryl.

Depending on the substituents, each of the carbon atoms in each of the compounds described above, namely $C_1$-Cn and Ca-Cm, can be chiral or non-chiral. Any chiral carbon atom that is present in the compounds described herein can be either in an R-configuration, an S-configuration or racemic. Thus present embodiments encompass any combination of chiral and racemic carbon atoms, including all the possible stereoisomers, optical isomers, enantiomers, and anomers. As is demonstrated in the Examples section that follows, the compounds of embodiments of the present invention can be synthesized while retaining a configuration of the starting material. The compounds of the present embodiments can be further selectively synthesized in terms of the stereochemistry of the oxidized group. Hence, by selecting the appropriate starting materials and the appropriate syntheses conditions, the optical purity (e.g., the inclusion of chiral and/or racemic carbons) and the obtained stereoisomers of the resulting compounds can be determined. In cases where racemic mixtures are obtained, known techniques can be used to separate the optical or stereo-isomers. Such techniques are described, for example, in "Organic chemistry, fourth Edition by Paula Yurkanis Bruice, page 180-185 and page 214, Prentice Hall, Upper Sadde River, N.J. 07458".

The present embodiments further encompass any pharmaceutically acceptable salts, prodrugs, hydrates and solvates of the compounds described hereinabove.

The term "prodrug" refers to an agent, which is converted into the active compound (the active parent drug) in vivo. Prodrugs are typically useful for facilitating the administration of the parent drug. They may, for instance, be bioavailable by oral administration whereas the parent drug is not. The prodrug may also have improved solubility as compared with the parent drug in pharmaceutical compositions. Prodrugs are also often used to achieve a sustained release of the active compound in vivo. An example, without limitation, of a prodrug would be a compound as described herein, having one or more carboxylic acid moieties, which is administered as an ester (the "prodrug"). Such a prodrug is hydrolysed in vivo, to thereby provide the free compound (the parent drug). The selected ester may affect both the solubility characteristics and the hydrolysis rate of the prodrug.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound. An example, without limitation, of a pharmaceutically acceptable salt would be a carboxylate anion and a cation such as, but not limited to, ammonium, sodium, potassium and the like.

The term "solvate" refers to a complex of variable stoichiometry (e.g., di-, tri-, tetra-, penta-, hexa-, and so on), which is formed by a solute (the compound of present embodiments) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

As is detailed hereinbelow, the newly designed compounds of present embodiments exert a highly beneficial immunomodulation activity and therefore can be utilized in various therapeutic applications. Utilizing these compounds in therapeutic application involves administration thereof either per se, or as a part of a pharmaceutical composition where it is mixed with suitable carriers or excipients.

Thus, according to another aspect of embodiments of the present invention, there is provided a pharmaceutical composition, which comprises, as an active ingredient, any of the compounds described herein in general formula I and the accompanying description, and a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the compounds (oxidized thiophospholipids, e.g., CI-211, CI-212 and other compounds depicted in the general formula I hereinabove) accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

In an optional embodiment of the present invention, the pharmaceutical compositions are designed for modulating an immune and/or inflammatory response via mucosal administration.

In another optional embodiment of the present invention, the pharmaceutical compositions are designed for modulating an immune and/or inflammatory response via oral administration.

Optionally, the pharmaceutical compositions of embodiments of the present invention are designed for nasal, or intraperitoneal administration, as is detailed hereinafter.

Pharmaceutical compositions of embodiments of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with present embodiments thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, for example, in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose; and/or physiologically acceptable polymers such as polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to embodiments of the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of embodiments of the present invention may also be formulated in rectal compositions such as suppositories or retention enemas, using, e.g., conventional suppository bases such as cocoa butter or other glycerides.

Pharmaceutical compositions suitable for use in context of the present embodiments include compositions wherein the active ingredients are contained in an amount effective to achieve the intended purpose. More specifically, a therapeutically effective amount means an amount of active ingredients effective to prevent, alleviate or ameliorate symptoms of a disorder (e.g., atherosclerosis) or prolong the survival of the subject being treated.

Determination of a therapeutically effective amount is well within the capability of those skilled in the art, especially in light of the detailed disclosure provided herein.

For any preparation used in the methods of embodiments of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures (e.g., as exemplified hereinbelow in the Examples section) or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See, e.g., Fingl, et al., 1975, in "The Pharmacological Basis of Therapeutics", Ch. 1 p. 1).

Dosage amount and interval may be adjusted individually to provide plasma or brain levels of the active ingredient are sufficient to induce or suppress angiogenesis (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of embodiments of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation described herein formulated in a compatible pharmaceutical carrier may also be prepared, placed in an appropriate container, and labeled for treatment of an indicated condition, as is further detailed hereinbelow.

Thus, in an optional embodiment of the present invention, the pharmaceutical composition is packaged in a packaging material and identified in print, on or in the packaging material, for use in the treatment or prevention of an inflammation associated with an endogenous oxidized lipid. A list of representative examples of diseases and disorders associated with such an inflammation is provided hereinbelow.

Alternatively or additionally, the pharmaceutical composition is packaged in a packaging material and identified in print, on or in the packaging material, for use in decreasing of a level of a cytokine selected from the group consisting of interleukin-12 and interleukin-23, and/or for use in the treatment of a disease or disorder in which decreasing a level of a cytokine selected from the group consisting of interleukin-12 and interleukin-23 is beneficial.

As is further described in detail hereinbelow, the pharmaceutical composition of present embodiments can further include an additional compound, which is useful in the treatment or prevention of the inflammation described herein.

As is described in detail in the Examples section that follows, representative examples of the newly designed compounds of embodiments of the present invention have been found effective in modulating a level of cytokines associated with an immune response and with inflammation. These results indicate that oxidized thiophospholipid analogs of endogenous oxidized lipids are effective for inhibiting an immune response and inflammation associated with an endogenous oxidized lipid.

Hence, according to another aspect of embodiments of the present invention there is provided a method of treating or preventing an inflammation associated with an endogenous oxidized lipid. The method according to this aspect of the present embodiments is effected by administering to a subject in need thereof a therapeutically effective amount of one or more oxidized thiophospholipids, for example, an oxidized thiophospholipid having the general formula I, as described herein.

As used herein, the phrase "an endogenous oxidized lipid" refers to one or more oxidized lipids that are present or formed in vivo, as a result of inflammatory and other cell- or humoral-mediated processes.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the phrase "treating or preventing" includes abrogating, substantially inhibiting, slowing or reversing the progression of a disease, substantially ameliorating clinical symptoms of a disease or substantially preventing the appearance of clinical symptoms of a disease.

Examples of subjects suitable for such treatment include subjects suffering from a disease or disorder associated with an inflammation, as is detailed hereinbelow. Suitable individual subjects according to present embodiments include mammals such as canines, felines, ovines, porcines, equines, and bovines. Optionally, the individual subjects according to the present embodiments are humans.

As used herein, the phrase "inflammation associated with an endogenous oxidized lipid" describes an inflammation that is associated with the in vivo formation or presence of one or more oxidized lipids (e.g., oxidized LDL, oxidized membrane lipids, etc.).

Inflammation is a protective response of the body to an injury. Several cytokines play key roles in mediating inflammatory reactions amongst which are interleukins 12 and 23 (IL-12 and IL-23). Excessive inflammation is oftentimes deleterious, involving or leading to a myriad of diseases and disorders. As is explained in detail hereinabove, excessive inflammatory response is typically associated with oxidized lipid epitopes.

Hence, according to optional embodiments of the present invention, there is provided a method of decreasing a level of a cytokine selected from the group consisting of interleukin-12 and interleukin-23 in a subject.

According to additional optional embodiments of the present invention, there is provided a method for treating a disease or disorder in which decreasing a level of a cytokine selected from the group consisting of interleukin-12 and interleukin-23 is beneficial.

The above methods are effected by administering to a subject in need thereof a therapeutically effective amount of one or more oxidized thiophospholipids, for example, an oxidized thiophospholipid having the general formula I, as described herein.

According to another aspect of embodiments of the present invention, there is provided a use of at least one oxidized thiophospholipid, for example, an oxidized thiophospholipid described herein, in the manufacture of a medicament. Optional formulations for a medicament are described herein.

In some embodiments, the medicament is for treating or preventing an inflammation associated with an endogenous oxidized lipid, as described in further detail herein.

In some embodiments, the medicament is for decreasing a level of a cytokine selected from the group consisting of interleukin-12 and interleukin-23 in a subject In some embodiments, the medicament is for treating a disease or disorder in which decreasing a level of a cytokine selected from the group consisting of interleukin-12 and interleukin-23 is beneficial.

The anti-inflammatory effect of oxidized thiophospholipids described herein may be utilized in treating or preventing inflammation-associated disease or disorders in which endogenous oxidized LDL or any other endogenous oxidized lipid is implicated. Such diseases and disorders include, for example, diseases or disorders associated with plaque formation, including but not limited to atherosclerosis, atherosclerotic cardiovascular disease, cerebrovascular disease, peripheral vascular disease, stenosis, restenosis and in-stent-stenosis, as well as autoimmune diseases or disorders, neurodegenerative diseases or disorders, proliferative disease or disorders and aging processes.

Thus, representative examples of diseases or disorders associated with an inflammation, which in turn is associated with an endogenous oxidized lipids, and are therefore treatable by the method of embodiments of the present invention include, for example, idiopathic inflammatory diseases or disorders, chronic inflammatory diseases or disorders, acute inflammatory diseases or disorders, autoimmune diseases or disorders, infectious diseases or disorders, inflammatory malignant diseases or disorders, inflammatory transplantation-related diseases or disorders, inflammatory degenerative diseases or disorders, diseases or disorders associated with a hypersensitivity, inflammatory cardiovascular diseases or disorders, inflammatory cerebrovascular diseases or disorders, peripheral vascular diseases or disorders, inflammatory glandular diseases or disorders, inflammatory gastrointestinal diseases or disorders, inflammatory cutaneous diseases or disorders, inflammatory hepatic diseases or disorders, inflammatory neurological diseases or disorders, inflammatory musculo-skeletal diseases or disorders, inflammatory renal diseases or disorders, inflammatory reproductive diseases or disorders, inflammatory systemic diseases or disorders, inflammatory connective tissue diseases or disorders, inflammatory tumors, necrosis, inflammatory implant-related diseases or disorders, inflammatory aging processes, immunodeficiency diseases or disorders, proliferative diseases and disorders and inflammatory pulmonary diseases or disorders, as is detailed hereinbelow.

Non-limiting examples of hypersensitivities include Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity, delayed type hypersensitivity, helper T lymphocyte mediated hypersensitivity, cytotoxic T lymphocyte mediated hypersensitivity, TH1 lymphocyte mediated hypersensitivity, and TH2 lymphocyte mediated hypersensitivity.

Non-limiting examples of inflammatory cardiovascular disease or disorder include occlusive diseases or disorders, atherosclerosis, a cardiac valvular disease, stenosis, restenosis, in-stent-stenosis, myocardial infarction, coronary arterial disease, acute coronary syndromes, congestive heart failure, angina pectoris, myocardial ischemia, thrombosis, Wegener's granulomatosis, Takayasu's arteritis, Kawasaki syndrome, anti-factor VIII autoimmune disease or disorder, necrotizing small vessel vasculitis, microscopic polyangiitis, Churg and Strauss syndrome, pauci-immune focal necrotizing glomerulonephritis, crescentic glomerulonephritis, antiphospholipid syndrome, antibody induced heart failure, thrombocytopenic purpura, autoimmune hemolytic anemia, cardiac autoimmunity, Chagas' disease or disorder, and anti-helper T lymphocyte autoimmunity.

Stenosis is an occlusive disease of the vasculature, commonly caused by atheromatous plaque and enhanced platelet activity, most critically affecting the coronary vasculature.

Restenosis is the progressive re-occlusion often following reduction of occlusions in stenotic vasculature. In cases where patency of the vasculature requires the mechanical support of a stent, in-stent-stenosis may occur, re-occluding the treated vessel.

Non-limiting examples of cerebrovascular diseases or disorders include stroke, cerebrovascular inflammation, cerebral hemorrhage and vertebral arterial insufficiency.

Non-limiting examples of peripheral vascular diseases or disorders include gangrene, diabetic vasculopathy, ischemic bowel disease, thrombosis, diabetic retinopathy and diabetic nephropathy.

Non-limiting examples of autoimmune diseases or disorders include all of the diseases caused by an immune response such as an autoantibody or cell-mediated immunity to an autoantigen and the like. Representative examples are chronic rheumatoid arthritis, juvenile rheumatoid arthritis, systemic lupus erythematosus, scleroderma, mixed connective tissue disease, polyarteritis nodosa, polymyositis/dermatomyositis, Sjogren's syndrome, Bechet's disease, multiple sclerosis, autoimmune diabetes, Hashimoto's disease, psoriasis, primary myxedema, pernicious anemia, myasthenia gravis, chronic active hepatitis, autoimmune hemolytic anemia, idiopathic thrombocytopenic purpura, uveitis, vasculitides and heparin induced thrombocytopenia.

Non-limiting examples of inflammatory glandular diseases or disorders include pancreatic diseases or disorders, Type I diabetes, thyroid diseases or disorders, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome.

Non-limiting examples of inflammatory gastrointestinal diseases or disorders include colitis, ileitis, Crohn's disease, chronic inflammatory intestinal disease, inflammatory bowel syndrome, chronic inflammatory bowel disease, celiac disease, ulcerative colitis, an ulcer, a skin ulcer, a bed sore, a gastric ulcer, a peptic ulcer, a buccal ulcer, a nasopharyngeal ulcer, an esophageal ulcer, a duodenal ulcer and a gastrointestinal ulcer.

Non-limiting examples of inflammatory cutaneous diseases or disorders include acne, an autoimmune bullous skin disease, pemphigus vulgaris, bullous pemphigoid, pemphigus foliaceus, contact dermatitis and drug eruption.

Non-limiting examples of inflammatory hepatic diseases or disorders include autoimmune hepatitis, hepatic cirrhosis, and biliary cirrhosis.

Non-limiting examples of inflammatory neurological diseases or disorders include multiple sclerosis, Alzheimer's disease, Parkinson's disease, myasthenia gravis, motor neuropathy, Guillain-Barre syndrome, autoimmune neuropathy, Lambert-Eaton myasthenic syndrome, paraneoplastic neurological disease or disorder, paraneoplastic cerebellar atrophy, non-paraneoplastic stiff man syndrome, progressive cerebellar atrophy, Rasmussen's encephalitis, amyotrophic lateral sclerosis, Sydeham chorea, Gilles de la Tourette syndrome, autoimmune polyendocrinopathy, dysimmune neuropathy, acquired neuromyotonia, arthrogryposis multiplex, Huntington's disease, AIDS associated dementia, amyotrophic lateral sclerosis (AML), multiple sclerosis, stroke, an inflammatory retinal disease or disorder, an inflammatory ocular disease or disorder, optic neuritis, spongiform encephalopathy, migraine, headache, cluster headache, and stiff-man syndrome.

Non-limiting examples of inflammatory connective tissue diseases or disorders include autoimmune myositis, primary Sjogren's syndrome, smooth muscle autoimmune disease or disorder, myositis, tendinitis, a ligament inflammation, chondritis, a joint inflammation, a synovial inflammation, carpal tunnel syndrome, arthritis, rheumatoid arthritis, osteoarthritis, ankylosing spondylitis, a skeletal inflammation, an autoimmune ear disease or disorder, and an autoimmune disease or disorder of the inner ear.

Non-limiting examples of inflammatory renal diseases or disorders include autoimmune interstitial nephritis and/or renal cancer.

Non-limiting examples of inflammatory reproductive diseases or disorders include repeated fetal loss, ovarian cyst, or a menstruation associated disease or disorder.

Non-limiting examples of inflammatory systemic diseases or disorders include systemic lupus erythematosus, systemic sclerosis, septic shock, toxic shock syndrome, and cachexia.

Non-limiting examples of infectious disease or disorder include chronic infectious diseases or disorders, a subacute infectious disease or disorder, an acute infectious disease or disorder, a viral disease or disorder, a bacterial disease or disorder, a protozoan disease or disorder, a parasitic disease or disorder, a fungal disease or disorder, a mycoplasma disease or disorder, gangrene, sepsis, a prion disease or disorder, influenza, tuberculosis, malaria, acquired immunodeficiency syndrome, and severe acute respiratory syndrome.

Non-limiting examples of inflammatory transplantation-related diseases or disorders include graft rejection, chronic graft rejection, subacute graft rejection, acute graft rejection hyperacute graft rejection, and graft versus host disease or disorder. Exemplary implants include a prosthetic implant, a breast implant, a silicone implant, a dental implant, a penile implant, a cardiac implant, an artificial joint, a bone fracture repair device, a bone replacement implant, a drug delivery implant, a catheter, a pacemaker, an artificial heart, an artificial heart valve, a drug release implant, an electrode, and a respirator tube.

Non-limiting examples of inflammatory tumors include a malignant tumor, a benign tumor, a solid tumor, a metastatic tumor and a non-solid tumor.

Non-limiting examples of inflammatory pulmonary diseases or disorders include asthma, allergic asthma, emphysema, chronic obstructive pulmonary disease or disorder, sarcoidosis and bronchitis.

An example of a proliferative disease or disorder is cancer.

The implication of phospholipids and phospholipid metabolites in treating of preventing diseases and syndromes such as, for example, oxidative stress of aging (Onorato J M, et al, Annal N Y Acad Sci 1998 Nov. 20; 854:277-90), rheumatoid arthritis (RA) (Paimela L, et al. Ann Rheum Dis 1996 August; 55(8):558-9), juvenile rheumatoid arthritis (Savolainen A, et al, 1995; 24(4):209-11), inflammatory bowel disease (IBD) (Sawai T, et al, Pediatr Surg Int 2001 May; 17(4): 269-74) and renal cancer (Noguchi S, et al, Biochem Biophys Res Commun 1992 Jan. 31; 182(2):544-50), has been reported, and thus further support the beneficial use of oxidized thiophospholipid analogs of oxidized phospholipids in the treatment or prevention of these diseases or disorders.

According to the method of embodiments of the present invention, the oxidized thiophospholipids can be administered to a subject by various routes, including, for example, the oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular routes. However, as is described in detail herein throughout and is further demonstrated in the Examples section that follows, preferred routes of administration include the oral, mucosal, nasal, intradermal (subcutaneous) and intraperitoneal routes.

Hence, in one embodiment, 0.1-100 mg/kg of an oxidized thiophospholipid as described herein is administered intraperitoneally, in a suitable carrier such as but not limited to PBS or glycerol, one to three times, every week, on a chronic or alternate regiment.

In another embodiment, 0.1-100 mg/kg of an oxidized thiophospholipid as described herein is administered nasally, in a suitable carrier such as but not limited to PBS or glycerol, one to three times, every week, on a chronic or alternate regiment.

In still another embodiment, 0.1-100 mg/kg of an oxidized thiophospholipid as described herein is administered subcutaneously, in a suitable carrier such as but not limited to PBS or glycerol, one to three times, every week, on a chronic or alternate regiment.

In yet another embodiment, 0.1-100 mg/kg of an oxidized thiophospholipid as described herein is administered orally, in a suitable carrier such as but not limited to PBS or glycerol, one to three times, every week, on a chronic or alternate regiment.

The pharmaceutical compositions and the methods described herein may further involve the administration of one or more additional compounds that are capable of treating or preventing an inflammation associated with endogenous oxidized lipid as delineated hereinabove.

The methods according to embodiments of the present invention can therefore involve co-administering, prior to, concomitant with or after the administration of the oxidized thiophospholipids, a therapeutically effective amount of one or more of such additional compounds, while the pharmaceutical composition according to the present embodiments may include, in addition to the compounds as described herein, such additional compounds.

Representative examples of additional compounds that are capable of treating or preventing an inflammation associated with endogenous oxidized lipid delineated hereinabove, and are therefore usable is the context of this embodiment of the present invention include, without limitation, HMGCoA reductase inhibitors (statins), mucosal adjuvants, corticosteroids, steroidal anti-inflammatory drugs, non-steroidal anti-inflammatory drugs, analgesics, growth factors, toxins, cholesteryl ester transfer protein (CETP) inhibitors, perixosomes, proliferative activated receptor (PPAR) agonists, anti-atherosclerosis drugs, anti-proliferative agents, ezetimide, nicotinic acid, squalene inhibitors, an ApoE Milano, HSPs, Beta-2-glycoprotein-I and any derivative and analog thereof.

HMGCoA reductase inhibitors (statins) are well known drugs that effectively reduce LDL-cholesterol levels by inhibiting the enzyme that regulates the rate of cholesterol production and increasing the clearance of LDL-cholesterol present in the blood by the liver. Non-limiting examples of commonly prescribed statins include Atorvastatin, Fluvastatin, Lovastatin, Pravastatin and Simvastatin.

Ezetimibe is the first of a new class of cholesterol absorption inhibitors that potently and selectively inhibits dietary and biliary cholesterol absorption at the brush border of the intestinal epithelium, without affecting the absorption of triglyceride or fat-soluble vitamins. Ezetimibe thus reduces overall cholesterol delivery to the liver, secondarily inducing increased expression of LDL receptors, resulting in an increased removal of LDL-C from the plasma.

Peroxisome is a single-membrane organelle present in nearly all eukaryotic cells. One of the most important metabolic processes of the peroxisome is the β-oxidation of long and very long chain fatty acids. The peroxisome is also involved in bile acid synthesis, cholesterol synthesis, plasmalogen synthesis, amino acid metabolism, and purine metabolism.

Nicotinic acid is a known agent that lowers total cholesterol, LDL-cholesterol, and triglyceride levels, while raising HDL-cholesterol levels. There are three types of nicotinic acid drugs: immediate release, timed release, and extended release. Nicotinic acid or niacin, the water-soluble B vitamin, improves all lipoproteins when given in doses well above the vitamin requirement.

Squalene, an isoprenoid compound structurally similar to beta-carotene, is an intermediate metabolite in the synthesis of cholesterol. In humans, about 60 percent of dietary squalene is absorbed. It is transported in serum generally in association with very low density lipoproteins and is distributed ubiquitously in human tissues, with the greatest concentration in the skin, where it is one of the major components of skin surface lipids. Squalene inhibitors (e.g., monooxygenase and synthase) serve as cholesterol biosynthesis inhibitors.

Proliferative Activated Receptor (PPAR) agonists, e.g., fibrates, are fatty acid-activated members of the nuclear receptor superfamily that play important roles in lipid and glucose metabolism, and have been implicated in obesity-related metabolic diseases such as hyperlipidemia, insulin resistance, and coronary artery disease. Fibrates are generally effective in lowering elevated plasma triglycerides and cholesterol and act as PPAR agonists. The most pronounced effect of fibrates includes a decrease in plasma triglyceride-rich lipoproteins (TRLs). Levels of LDL cholesterol (LDL-C) generally decrease in individuals with elevated baseline plasma concentrations, and HDL cholesterol (HDL-C) levels are usually increased when baseline plasma concentrations are low. Non-limiting examples of commonly prescribed fibrates include bezafibrate, gemfibrozil and fenofibrate.

Cholesteryl Ester Transfer Protein (CETP) inhibitors play a major role in atherogenesis, by reducing cholesteryl ester accumulation within macrophages and the arterial wall, and thus reducing foam cell formation and affecting the cholesterol absorption. The most promising presently known CETP inhibitor is avisimibe.

ApoA-I Milano is typically used as a recombinant complex with phospholipid (ETC-216) and produces significant regression of coronary atherosclerosis.

Co-administration of mucosal adjuvants has been shown to be highly beneficial for preventing the invasion of infectious agents through mucosal surfaces. In the early stages of induction of mucosal immune response, the uptake of orally or nasally administered antigens is achieved through a unique set of antigen-sampling cells, M cells located in follicle-associated epithelium (FAE) of inductive sites. After successful uptake, the antigens are immediately processed and presented by the underlying dendritic cells (DCs).

Non-limiting examples of non-steroidal anti-inflammatory drugs include oxicams, such as piroxicam, isoxicam, tenoxicam, sudoxicam, and CP-14,304; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone.

Non-limiting examples of steroidal anti-inflammatory drugs include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

Non-limiting examples of analgesics (pain relievers) include aspirin and other salicylates (such as choline or magnesium salicylate), ibuprofen, ketoprofen, naproxen sodium, and acetaminophen.

Growth factors are hormones which have numerous functions, including regulation of adhesion molecule production, altering cellular proliferation, increasing vascularization, enhancing collagen synthesis, regulating bone metabolism and altering migration of cells into given area. Non-limiting examples of growth factors include insulin-like growth factor-1 (IGF-1), transforming growth factor-β (TGF-β), a bone morphogenic protein (BMP) and the like.

Non-limiting examples of toxins include the cholera toxin, which also serves as an adjuvant.

Non-limiting examples of anti-proliferative agents include an alkylating agent such as a nitrogen mustard, an ethylenimine and a methylmelamine, an alkyl sulfonate, a nitrosourea, and a triazene; an antimetabolite such as a folic acid analog, a pyrimidine analog, and a purine analog; a natural product such as a vinca alkaloid, an epipodophyllotoxin, an antibiotic, an enzyme, a taxane, and a biological response modifier; miscellaneous agents such as a platinum coordination complex, an anthracenedione, an anthracycline, a substituted urea, a methyl hydrazine derivative, or an adrenocortical suppressant; or a hormone or an antagonist such as an adrenocorticosteroid, a progestin, an estrogen, an antiestrogen, an androgen, an antiandrogen, or a gonadotropin-releasing hormone analog. Specific examples of chemotherapeutic agents include, for example, a nitrogen mustard, an epipodophyllotoxin, an antibiotic, a platinum coordination complex, bleomycin, doxorubicin, paclitaxel, etoposide, 4-OH cyclophosphamide, and cisplatinum.

The HSP family consists of approximately 25 proteins discerned by their molecular weights with highly conserved structures. Almost all humans have cellular and humoral immune reactions against microbial heat-shock protein 60 (HSP60). Because a high degree of antigenic homology exists between microbial (bacterial and parasitic) and human HSP60, the 'cost' of immunity to microbes might be the danger of cross-reactivity with human HSP60 expressed by the endothelial cells of stressed arteries. Genuine autoimmunity against altered autologous HSP60 might trigger this process also (Wick et al. Atherosclerosis as an autoimmune disease: an update. TRENDS in Immunology. 2001; 22(12):665-669). HSP has been implicated as a target autoantigen in several experimental autoimmune diseases (arthritis, type I diabetes). Anti-HSP65 as well as anti-HSP60 antibodies have been demonstrably associated with atheromatous lesions in humans. Studies conducted in rabbits and mice show that the generation of an HSP65-induced immune response by immunization with the recombinant protein or with an HSP65-rich preparation of *Mycobacterium tuberculosis* enhances atherogenesis. As autoimmune processes pointing to HSP65 as a possible antigenic candidate, creating a state of unresponsiveness by induction of mucosal "tolerization" has been employed in order to block these responses, our group reported that early atherosclerosis was attenuated in HSP65-fed mice, compared with either BSA or PBS fed mice (Harats et al. Oral tolerance with heat shock protein 65 attenuates *mycobacterium tuberculosis* induced and high fat diet driven atherosclerosis lesions. J Am Coll Cardiol. 2002; 40:1333-1338), this was further supported by Maron who demonstrated that nasal vaccination with HSP reduces the inflammatory process associated with atherosclerosis (Maron et al. Mucosal administration of heat shock protein-65 decreases atherosclerosis and inflammation in aortic arch of low density lipoprotein receptor-deficient mice. Circulation. 2002; 106: 1708-1715).

Beta-2-glycoprotein I (beta2GPI) is a phospholipid binding protein shown to serve as a target for prothrombotic antiphospholipid antibodies. It has recently been demonstrated to drive an immune mediated reaction and enhance murine atherosclerosis. β-Antibodies to beta-2-GPI have the ability to activate monocytes and endothelial cells and can induce an immune response to beta2GPI in atherosclerosis-prone mice accelerated atherosclerosis. When beta2GPI-reactive lymph node and spleen cells were transferred to LDL-receptor-deficient mice they promoted fatty streak formation, proving a direct proatherogenic role for beta2GPI-specific lymphocytes. Inducing immunological tolerance to beta2GPI by prior oral feeding with the antigen resulted in a significant reduction in the extent of atherosclerotic lesions. Thus, beta2GPI is a candidate player in the atherosclerotic plaque, and can possibly be employed as an immunomodulator of plaque progression. Oral feeding with of beta2GPI inhibited lymph node cell reactivity to beta2GPI in mice immunized against the human protein. IL-4 and IL-10 production was upregulated in lymph node cells of beta2GPI-tolerant mice immunized against beta2GPI, upon priming with the respective protein. Thus, oral administration of beta2GPI is an effective means of suppressing atherogenesis in mice (George et al. Suppression of early atherosclerosis in LDL-receptor deficient mice by oral tolerance with beta2-glycoprotein I. Cardiovasc Res. 2004; 62(3):603-9).

The oxidized thiophospholipids described herein may be prepared according to any suitable method know in the chemical arts. However, the present inventors have uncovered a simple and convenient method for producing oxidized thiophospholipids as described herein, by introducing a thiophosphate moiety into a lipid or lipid analog.

Thus, according to another aspect of embodiments of the present invention, there is provided a method of introducing a thiophosphate moiety into a compound so as to produce an oxidized thiophosphate compound as described herein, the method being effected by:

reacting a thiophosphorus-containing compound having a second reactive group and a third reactive group with a compound having the general formula VI:

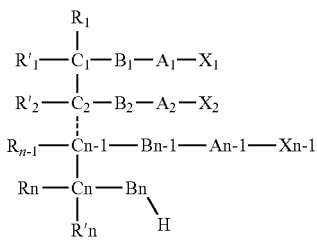

Formula VI wherein:

n is an integer of 1-6, whereas if n=1, Cn, Rn and R'n are absent, and $C_1$ is attached to Bn;

each of $B_1, B_2, \ldots Bn-1$ and Bn is independently selected from the group consisting of oxygen, sulfur, nitrogen, phosphorus and silicon, whereby each of the nitrogen, phosphorus and silicon is substituted by at least one substituent selected from the group consisting of hydrogen, lone pair electrons, alkyl, halo, cycloalkyl, aryl, hydroxy, thiohydroxy, alkoxy, aryloxy, thioaryloxy, thioalkoxy and oxo;

each of $A_1, A_2, \ldots An-1$ is independently selected from the group consisting of CR"R''', C=O and C=S; and each of $X_1, X_2, \ldots Xn-1$ is independently a saturated or unsaturated hydrocarbon having the general formula II:

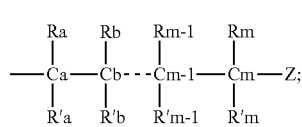

Formula II wherein:
m is an integer of 1-26; and
Z is selected from the group consisting of:
H,

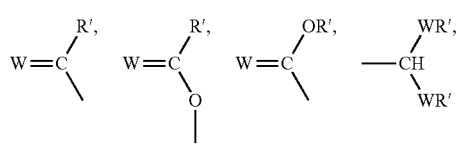

—OH and a pre-oxidized moiety,
whereas:

W is selected from the group consisting of oxygen, sulfur, nitrogen and phosphorus, whereby each of the nitrogen and phosphorus is substituted by at least one substituent selected from the group consisting of hydrogen, lone pair electrons, alkyl, halo, cycloalkyl, aryl, hydroxy, thiohydroxy, alkoxy, aryloxy, thioaryloxy, thioalkoxy and oxo;

R' is selected from the group consisting of alkyl, cycloalkyl, aryl and heteroaryl; and in at least one of $X_1, X_2, \ldots Xn-1$, Z is not hydrogen; and wherein:

each of $R_1, R'_1, R_2, \ldots Rn-1, Rn, R'n$, each of R" and R''' and each of Ra, R'a, Rb, R'b, ... Rm-1, R'm-1, Rm and R'm is independently selected from the group consisting of hydrogen, a bond, alkyl, alkenyl, alkylnyl, cycloalkyl, aryl, heteroaryl, heteroalicyclic, halo, trihalomethyl, hydroxy, alkoxy, aryloxy, thiohydroxy, thioalkoxy, thioaryloxy, phosphonate, thiophosphonate, phosphate, thiophosphate, phosphinyl, sulfonyl, sulfinyl, sulfonamide, amide, carbonyl, thiocarbonyl, C-carboxy, O-carboxy, O-carbamate, N-carbamate, C-thiocarboxy, S-thiocarboxy and amino, or, alternatively, at least two of $R_1, R'_1, R2, \ldots Rn-1, Rn$ and R'n and/or at least two of Ra, R'a, Rb, R'b, ... Rm-1, R'm-1, Rm and R'm form at least one four-, five- or six-membered aromatic, heteroaromatic, alicyclic or heteroalicyclic ring; and each of $C_1, C_2, \ldots, Cn-1, Cn$, and each of Ca, Cb, Cm-1 and Cm is a chiral or non-chiral carbon atom, whereby each chiral carbon atom has a S-configuration and/or a R-configuration, or a pharmaceutically acceptable salt, a prodrug, a hydrate or a solvate thereof, the second reactive group being capable of reacting with Bn, to thereby provide a compound having a reactive thiophosphorus-containing group attached to Bn; and converting the reactive thiophosphorus-containing group to the thiophosphate moiety, to thereby produce an oxidized thiophospholipid.

When Z in Formula V is pre-oxidized moiety, the method further comprises oxidizing the pre-oxidized moiety to thereby produce an oxidized thiophospholipid.

As used herein, the phrase "pre-oxidized moiety" refers to any moiety which is capable of reacting with an oxidizing agent so as to generate one or more oxidized groups such as, for example, H,

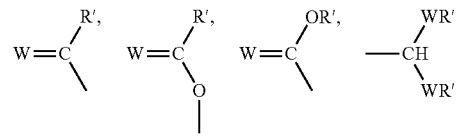

and —OH (as defined hereinabove).

The oxidation of a pre-oxidized moiety to form an oxidized group can be performed before or after introduction of the thiophosphate moiety.

Methods and procedures for oxidizing a pre-oxidized moiety to an oxidized group to thereby produce an oxidized phospholipid are described in detail in U.S. patent application Ser. No. 11/650,973 (Publication No. 2007-0112211). One of ordinary skill in the art will be capable of incorporating the procedures described therein for producing an oxidized group in the method described herein for producing an oxidized thiophospholipid.

In some embodiments, the pre-oxidized moiety is an unsaturated alkyl (e.g., an alkenyl comprising 2 carbon atoms, for example, $CH_2=CH-$).

In some embodiments, Bn is oxygen or sulfur, such that the second reactive group being capable of reacting with Bn is a reactive group capable of reacting with a hydroxy and/or thiohydroxy group.

Optionally, the hydroxy or thiohydroxy group (Bn-H), as be protected by a suitable protecting group prior to being reacted with the thiophosphorous-containing compound. The protecting group can be removed prior to, or concomitant with, reacting the compound having Formula VI with the thiophosphorous-containing compound.

As used herein, the phrase "thiophosphorus-containing compound" refers to a compound comprising phosphorus bound to at least one sulfur atom, optionally via a double bond. $PSCl_3$ is an exemplary thiophosphorus-containing compound.

In some embodiments, for example, when the thiophosphorus-containing compound is $PSCl_3$, the above-described thiophosphorus-containing group formed from the thiophosphorus-containing compound is a dichlorothiophosphate group (—P(=S)Cl$_2$).

Optionally, reacting the thiophosphorus-containing compound with the compound having general formula VI is performed in the presence of a base (e.g., a tertiary amine such as a trialkylamine).

According to optional embodiments, the compound having the general formula VI has the saturated or unsaturated hydrocarbon having the above general formula II attached thereto via an ether bond (e.g., the compound is an etherified lipid analog, as described hereinabove).

In some embodiments, the thiophosphate moiety is thiophosphoric acid and converting the reactive thiophosphorus-containing group to the thiophosphate moiety comprises hydrolyzing the reactive thiophosphorus-containing group (e.g., such that reactive groups in the thiophosphorus-containing group are converted to —OH).

In alternative embodiments, the thiophosphate moiety comprises an alkylamino group and converting the reactive thiophosphorus-containing group to the thiophosphate moiety comprises reacting the reactive thiophosphorus-containing moiety with a derivative of an aminoalkyl, the derivative being capable of reacting with the reactive thiophosphorus-containing group. Suitable aminoalkyl derivatives include, for example, amino alcohols (e.g., an amino alcohol described hereinabove), in which case the reactive groups in the thiophosphorus-containing group are optionally converted to amino-substituted alkoxy).

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions illustrate some embodiments of the invention in a non-limiting fashion.

Materials and Methods

Materials:

Acetic acid (glacial) was obtained from Bio-Lab;

Crystal violet was obtained from Sigma;

Fetal bovine serum (heat inactivated) was obtained from Biological Industries (Israel);

Methanol (absolute) was obtained from Bio-Lab;

Mouse GM-CSF (granulocyte-macrophage colony-stimulating factor) was obtained from Peprotech (Israel);

Penicillin/streptomycin solution was obtained from Biological Industries (Israel);

Red blood cell lysis buffer was obtained from Biological Industries (Israel); and RPMI-1640 medium with L-glutamine was obtained from Biological Industries (Israel).

COSTAR® Sterile 24-well tissue culture treated plates were obtained from Corning.

Phosphate buffered saline (PBS) was prepared by diluting Dulbecco's phosphate buffered saline 10× concentrate without calcium or magnesium (Biological Industries, Israel) with double-distilled water.

Cells were incubated at 37° C. in an atmosphere with 5% $CO_2$.

Spectrometric measurements were performed using a Tecan SUNRISE plate reader and Magellan Version 6.3 data acquisition software. Absorption at 595 nm was determined using a Tecan SpectraFluor 595 nm band-pass filter.

For in vitro studies, the tested compounds were dissolved in ethanol to a concentration of 100 mg/ml and then diluted in PBS to a concentration of 1 mg/ml.

Tyrosine Phosphorylation Assay:

Thioglycollate stimulated mouse macrophages were treated for 10 minutes with 20 µg/ml of the tested compound in phosphate buffered saline (PBS) with 1% ethanol. Treatment with either 20 µg/ml of phosphatidylcholine or solvent (PBS with 1% ethanol) was used as a negative control. Treatment with 20 µg/ml CI-201 (1-hexadecyl-2-(4'-carboxy)butyl-sn-glycero-3-phosphothiocholine) was used as a positive control.

Proteins with phosphorylated tyrosine were then observed by Western blot, using a monoclonal anti-phosphotyrosine antibody. Western blotting for ERK1/2 was performed as a control for protein loading.

In Vitro Toxicity Assay:

Thioglycollate-elicited mouse peritoneal macrophages were washed, counted and seeded ($5 \times 10^5$ cells per well in 24-well plates) in triplicate wells in medium containing RPMI-1640, L-glutamine, 10% fetal calf serum (FCS) and antibiotics (penicillin/streptomycin). After a recovery period of 24 hours, the tested compound (or controls) was added to the cell medium at doses of 2, 10, 20, 50, 100 or 150 µg/ml, keeping the added volume equal in all treatments by complementing the volume with solvent.

Following addition of the compounds, the cells were incubated for an additional 24 hours, after which the cells were washed, fixed with a solution of 10% methanol/10% acetic acid and stained with crystal violet (0.4% in 20% ethanol). Cell numbers were measured by determining optical density at 595 nm. Cells incubated with vehicle (PBS with 1% ethanol) were used as a control, to which cell numbers in treated samples were normalized. Each experiment was performed three times.

Growth conditions were considered to be adequate by confirming that cell numbers in vehicle-treated cells did not decrease over the course of the 24 hours.

In Vitro IL12/23p40 Assay:

Bone marrow derived cells (BMDCs) were obtained from the femur and tibia of female C57BL mice. Bone-marrow was flushed out femur and tibia with cold RPMI-1640. A cell suspension was prepared, and erythrocytes were removed using red blood cell (RBC) lysis buffer. Cells were washed in PBS, and incubated at 4° C. for 15 minutes in a buffer containing PBS and 0.5% bovine serum albumin (BSA) with mouse B220 and CD90 microbeads (Miltenyi Biotech, Germany). Cells were then washed, resuspended in the same buffer, and depleted from B and T cells on a Midi-Macs separation unit through a LD or LS column (Miltenyi Biotech). The cells were prepared freshly for each experiment.

The depleted bone marrow cells were counted, washed and seeded at a concentration of $10^6$ cells/ml in medium containing RPMI-1640, L-glutamine, β-mercaptoethanol, 10% fetal calf serum (FCS), antibiotics (penicillin/streptomycin) and 20 ng/ml of mouse GM-CSF (granulocyte-macrophage colony-stimulating factor). Medium was replaced every other day. On days 5-6 post culturing, cells were collected, counted and seeded at a concentration of $10^6$ cells/ml in the above medium. CI-211 was then added for 1 hour. The cells were activated for IL12/23p40 production by incubation for 24 hours with 10 µg/ml peptidoglycan (PGN). Cytokine production from the supernatant was measured by ELISA. Activated cells without CI-211 were used as the control.

Example 1

Preparation of exemplary oxidized thiophospholipids (CI-211 and CI-212)

Synthesis of 1-Hexadecyl-glycerol: A mixture of 40 ml (R)-(−)-2,2 dimethyl-1,3-dioxolane-4-methanol, 55 grams of powdered potassium hydroxide and 109 ml hexadecyl bromide were added to 500 ml benzene, and the reaction mixture was stirred and refluxed for 6 hours, while removing the water formed by azeotropic distillation. The volume of the solvent was gradually reduced to about 150 ml. The reaction mixture was then cooled to room temperature and stirred at this temperature overnight. Thereafter, 150 ml water was added, and the obtained mixture was extracted thrice with 150 ml diethyl ether. The combined organic phase was washed with 150 ml water and the solvent was then removed under reduced pressure. The residue was dissolved in 200 ml of a mixture of 90:10:5 (volume/volume) methanol:water:concentrated HCl, and the resulting solution was refluxed for 2 hours. After cooling to room temperature and adding 200 ml water, the product was extracted with 250 ml chloroform. The organic phase was washed consecutively with 250 ml water, 200 ml saturated aqueous solution of sodium carbonate, and again with 200 ml water. The solvent was removed under reduced pressure and the product was then crystallized from hexane (500 ml) to give 81.25 grams (yield 79%) of pure 1-hexadecyl-glycerol, which was dried in a desiccator under reduced pressure.

Synthesis of 1-Hexadecyl-3-trityl-sn-glycerol 40 grams of 1-hexadecyl-glycerol and 43 grams triphenylchloromethane were added to a mixture of 500 ml dry tetrahydrofuran and 130 ml dry acetonitrile. 35 ml of dry triethylamine was added, and the reaction mixture was refluxed for 17 hours. The reaction mixture was then cooled to room temperature, poured on ice (1 kilogram) and extracted thrice with 250 ml diethyl ether. The organic phase was washed consecutively with 100 ml water, 100 ml dilute (1.5%) sulfuric acid, 100 ml water, 100 ml concentrated aqueous sodium bicarbonate and again with 100 ml water. The obtained organic phase was dried over anhydrous sodium sulfate and the solvent was thereafter removed under reduced pressure. The residue was dissolved in 200 ml ethyl acetate and the resulting solution was cooled at −20° C. overnight. The mixture was then centrifuged at −5° C. and the mother liquid solution was poured off. The solid was dissolved in hexane and refrigerated overnight at 5° C. Filtration of the precipitate yielded pure 1-hexadecyl-3-trityl-sn-glycerol.

Synthesis of 1-Hexadecyl-2-(5'-hexenyl)-3-trityl-sn-glycerol 25 grams of 1-hexadecyl-3-trityl-sn-glycerol, 10 grams of powdered potassium hydroxide and 9.58 grams 5-hexenyl-1-methane sulfonate were added to 200 ml benzene, and the reaction mixture was stirred and refluxed for 8 hours, while removing the water formed by azeotropic distillation. The volume of the solvent was gradually reduced to about 50 ml. The reaction mixture was then cooled to room temperature and 150 ml water was added. The mixture was transferred to a separatory funnel and extracted thrice with 100 ml diethyl ether. The combined organic phase was washed thrice with 100 ml water, dried over anhydrous $Na_2SO_4$, and the solvent was then removed under reduced pressure, yielding 25 grams of 1-hexadecyl-2-(5'-hexenyl)-3-trityl-sn-glycerol (25 grams) as a light yellow oil.

Synthesis of 1-Hexadecyl-2-(4-carboxy)butyl-3-sn-glycerol 66.07 grams $NaIO_4$ was dissolved in 220 ml water, 3.17 grams $NaHCO_3$ and 1.09 gram $KMnO_4$ were added to the solution, and the obtained suspension was heated to a temperature of 40° C. A solution of 22 grams 1-hexadecyl-2-(5'-hexenyl)-3-trityl-sn-glycerol in 220 ml tert-butanol was added dropwise over the course of 1 hour, and the mixture was heated for an additional 1.5 hours. An additional 0.3 gram $KMnO_4$ was added, maintaining a pink color, and the mixture was heated for an additional 1.5 hours. The reaction mixture was then cooled to room temperature, transferred to a separatory funnel and extracted with 100 ml hexane. The organic phase was washed with a solution of 7.5 grams $Na_2S_2O_5$ in 50 ml water and then acidified to a pH of 1 by addition of 6 ml water with 0.3 ml concentrated HCl. The organic phase was concentrated by removal of about 100 ml solvent under reduced pressure. The remaining solution was heated to a temperature of 80° C. for 6 hours and then concentrated again by removal of about 125 ml solvent under reduced pressure. The pH of the residue was adjusted to pH 12 by adding 50 ml water and 5 ml of a 30% NaOH solution. The precipitate was filtered off and the filtrate was then extracted twice with 25 ml of a 1:1 (v/v) mixture of hexane:ethyl acetate. The aqueous phase containing the sodium salt of 1-hexadecyl-2-(4'-carboxy)butyl-3-trityl-sn-glycerol was acidified to pH 1 by addition of 4.5 ml concentrated HCl and was thereafter extracted twice with 50 ml hexane. After removal of the solvent under reduced pressure and overnight recrystallization of the crude product from 1:9 (v/v) acetone:hexane at 0° C., 9.2 grams of pure 1-hexadecyl 2 (4 carboxy)butyl-3-trityl-sn-glycerol was obtained (64.5% yield).

Synthesis of 1-Hexadecyl-2-(4-methylcarboxy)butyl-sn-glycerol 15.75 grams 1-hexadecyl-2-(4-carboxy)butyl-3-trityl-sn-glycerol was dissolved in 100 ml methanol. 20 ml of concentrated HCl (37%) was added and the reaction mixture was refluxed for 4 hours. The reaction mixture was then cooled to room temperature and stirred at room temperature overnight. The mixture was thereafter poured on ice (100 grams) and extracted thrice with 100 ml diethyl ether. The combined organic phase was then washed sequentially with 100 ml water, 100 ml saturated sodium bicarbonate solution, and 100 ml water, and then dried over anhydrous $Na_2SO_4$. The solvent was removed under reduced pressure, yielding 14 grams of 1-hexadecyl-2-(4-methylcarboxy)butyl-sn-glycerol as a yellow oil (86% yield).

Synthesis of 1-Hexadecyl-2-(4-methylcarboxy)butyl-sn-glycero-3-β-thiophosphorylethanolamine 2 ml triethylamine was added to a solution of 2 grams 1-hexadecyl-2-(4-methylcarboxy)butyl-sn-glycerol in 30 ml tetrahydrofuran. This solution was added dropwise over the course of 30 minutes to an ice-cooled solution of 1.50 ml phosphorus thiochloride in 20 ml tetrahydrofuran. The reaction mixture was then stirred in an ice bath for 10 minutes, and for additional 45 minutes at room temperature. The reaction mixture was cooled in an ice bath, and a solution of 845 µl ethanolamine and 4 ml triethylamine in 50 ml tetrahydrofuran was added dropwise over the course of 30 minutes. The stirring was continued for 10 minutes in the ice bath and further continued at room temperature overnight. The reaction mixture was filtered and the solvent from the filtrate was then removed under reduced pressure. The residue was dissolved in a mixture of 24 ml acetic acid and 10 ml water and heated to a temperature of 70° C. for 1 hour. After cooling, the reaction mixture was extracted thrice with 50 ml chloroform), the combined organic phase was washed twice with 50 ml water, and the solvent was then removed under reduced pressure, yielding 2.6 grams of 1-hexadecyl-2-(4-methylcarboxy)butyl-sn-glycero-3-O-thiophosphorylethanolamine as a brown oil.

Synthesis of 1-Hexadecyl-2-(4-carboxy)butyl-sn-glycero-3-β-thiophosphorylethanolamine (CI-212)

600 mg of 1-hexadecyl-2-(4-methylcarboxy)butyl-sn-glycero-3-O-thiophosphorylethanolamine was dissolved in 20 ml of an 8:2 (v/v) mixture of methanol: aqueous 10% NaOH. The obtained mixture was stirred at room temperature overnight. The pH of the reaction mixture was adjusted to pH 4 by adding formic acid. 50 ml water and 50 ml chloroform were thereafter added, the phases were then separated, and the aqueous phase was extracted with 50 ml chloroform. The combined organic phase was dried over $Na_2SO_4$ and the solvent was removed under reduced pressure. The crude product, CI-212, was purified by chromatography on a silica gel (10 grams). 60 mg of pure 1-hexadecyl-2-(4-carboxy)butyl-sn-glycero-3-O-thiophosphorylethanolamine was obtained by elution from the column with chloroform, followed by a mixture of chloroform, methanol and water. The yield for this step was 10%.

NMR Characterization of CI-212:

A sample of CI-212 was dissolved in deuterated chloroform ($CDCl_3$) with a few drops of deuterated methanol. The spectra were then measured at 300 MHz. Samples were measured by both $^1H$ and $^{13}C$ NMR spectroscopy.

The results showed the expected signals for the structural elements of 1-hexadecyl-2-(4-carboxy)butyl-sn-glycero-3-O-thiophosphorylethanolamine (CI-212) and thus fully supported the structure.

The assignment of the observed $^1H$ peaks according to the structure of 1-hexadecyl-2-(4-carboxy)butyl-sn-glycero-3-O-thiophosphorylethanolamine was as follows.

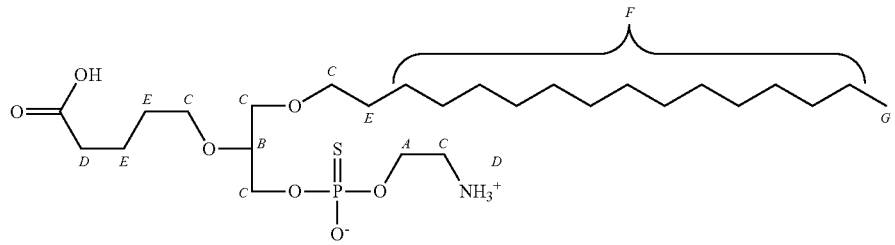

$^1H$ NMR (300 MHz, reference solvent ($CDCl_3$)=7.29 ppm)

| δ [ppm] | Description | Assignment (see formula above) |
|---|---|---|
| 4.18 | 2 H, br, s | A |
| 3.92 | 1 H, m | B |
| 3.42-3.67 | 10 H, m, 5 × $CH_2$ | C |
| 2.35 | 2 H, t, J = 7.5 Hz | D |
| 1.54-1.71 | 6 H, m, 3 × $CH_2$ | E |
| 1.256 | 26 H, m, 13 × $CH_2$ | F |
| 0.90 | 3 H, t, 1 × $CH_3$, J = 6.6 Hz | G |

The assignment of the observed $^{13}C$ peaks according to the structure of 1-hexadecyl-2-(4-carboxy)butyl-sn-glycero-3-O-thiophosphorylethanolamine was as follows:

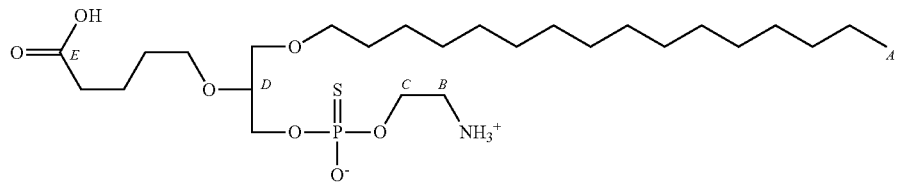

$^{13}C$ NMR (300 MHz, reference solvent ($CDCl_3$)=77.474 ppm)

| δ [ppm] | Assignment (see formula above) |
|---|---|
| 176.983 | E |
| 78.057 | D |
| 72.052 | |
| 70.681 | |
| 70.056 | |
| 65.924 | |
| 61.856 | C |
| 40.665 | B |
| 33.967 | |
| 32.117 | |
| 29.889 | |
| 29.720 | |
| 29.552 | |
| 29.396 | |
| 26.250 | |

| δ [ppm] | Assignment (see formula above) |
|---|---|
| 22.864 | |
| 21.829 | |
| 14.193 | A |

Mass Spectrometry Characterization of CI-212:

The calculated mass for 1-hexadecyl 2 (4 carboxy)butyl sn glycero-3-O-thiophosphorylethanolamine (CI-212) ($C_{26}H_{54}NO_7PS$) was 555.7482.

The mass spectrum performed using Electrospray Ionization Mass Spectrometry ($ES^-MS$) showed a molecular ion with m/z=554, corresponding to the deprotonated molecular ion $[M-H]^-$. The mass spectrometry spectrum is thus in agreement with the chemical structure of 1-hexadecyl 2 (4 carboxy)butyl sn glycero-3-O-thiophosphorylethanolamine.

Synthesis of 1-Hexadecyl-2-(4-carboxy)butyl-sn-glycero-3-thiophosphorylcholine (CI-211)

2 grams of 1-hexadecyl-2-(4-methylcarboxy)butyl-sn-glycero-3-O-thiophosphorylethanolamine was dissolved in a mixture of 60 ml methanol and 18 ml dichloromethane. This solution was heated to a temperature of 35° C., and a solution of 2.5 grams potassium carbonate in 10 ml water was then added dropwise while maintaining the solution at a temperature in a range of 35-40° C. The reaction mixture was stirred for 10 minutes and a solution of 1.7 ml dimethylsulfate in 10 ml methanol was then added dropwise. The reaction mixture was then stirred at 40° C. for 2 hours, cooled to room temperature, and stirred at room temperature overnight. 50 ml water was added, and the mixture was extracted thrice with 50 ml chloroform. The combined organic phase was washed with 50 ml water, and the solvent was removed under reduced pressure. The residue (1.6 gram) was dissolved in 50 ml of an 8:2 (v/v) mixture of methanol:aqueous 10% NaOH, and the obtained mixture was stirred at room temperature overnight. The pH of the reaction mixture was adjusted to pH 4 by addition of sodium dihydrogen phosphate followed by formic acid. 50 ml water and 50 ml chloroform were thereafter added, the phases were separated, and the aqueous phase was extracted with 50 ml chloroform. The combined organic phase was then dried over $Na_2SO_4$ and the solvent was removed under reduced pressure. The crude product, CI-211, was purified by chromatography on a silica gel (26 grams). 93 mg of pure 1-hexadecyl-2-(4-carboxy)butyl-sn-glycero-3-thiophosphorylcholine was obtained by elution from the column with chloroform, a mixture of chloroform and methanol, a mixture of chloroform, methanol and water.

NMR Characterization of CI-211:

A sample of CI-211 was dissolved in deuterated chloroform ($CDCl_3$) with a few drops of deuterated methanol. The spectra were then measured at 300 MHz. Samples were measured by both $^1H$ and $^{13}C$ NMR spectroscopy.

The results showed the expected signals for the structural elements of 1-hexadecyl-2-(4-carboxy)butyl-sn-glycero-3-thiophosphorylcholine (CI-211) and thus fully supported the structure.

The assignment of the observed $^1H$ peaks according to the structure of 1-hexadecyl-2-(4-carboxy)butyl-sn-glycero-3-thiophosphorylcholine was as follows.

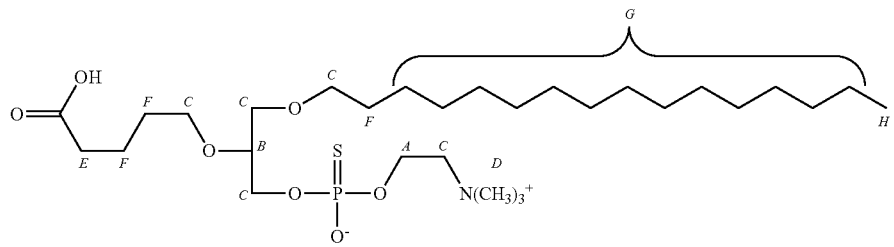

$^1H$ NMR (300 MHz, reference solvent ($CDCl_3$)=7.25 ppm)

| δ [ppm] | Description | Assignment (see formula above) |
|---|---|---|
| 4.282 | 2 H, br, s | A |
| 3.942-3.957 | 1 H, m | B |
| 3.415-3.689 | 10 H, m, 5 × $CH_2$ | C |
| 3.375 | 9 H, s, 3 × $CH_3$ | D |
| 2.302 | 2 H, m | E |
| 1.540-1.672 | 6 H, m, 3 × $CH_2$ | F |
| 1.255 | 26 H, m, 13 × $CH_2$ | G |
| 0.880 | 3 H, t, 1 × $CH_3$, J = 6.45 Hz | H |

The assignment of the observed $^{13}C$ peaks according to the structure of 1-hexadecyl-2-(4-carboxy)butyl-sn-glycero-3-thiophosphorylcholine was as follows:

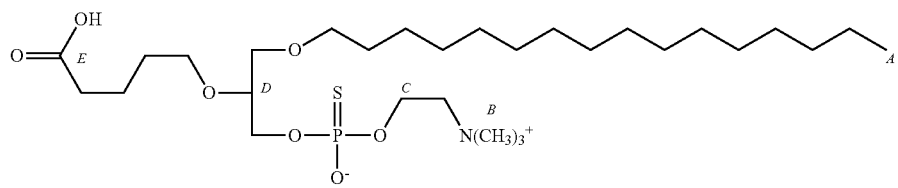

$^{13}$C NMR (300 MHz, reference solvent (CDCl$_3$)=77.190 ppm)

| δ [ppm] | Assignment (see formula above) |
|---|---|
| 177.823 | E |
| 77.984 | D |
| 71.894 | |
| 70.480 | |
| 70.191 | |
| 69.893 | |
| 65.889 | |
| 59.323 | C |
| 54.429 | B |
| 35.137 | |
| 34.989 | |
| 31.983 | |
| 29.762 | |
| 29.593 | |
| 29.419 | |
| 26.113 | |
| 22.740 | |
| 22.305 | |
| 14.132 | A |

Mass Spectrometry Characterization of CI-211:

The calculated mass for 1-hexadecyl-2-(4-carboxy)butyl-sn-glycero-3-thiophosphorylcholine (CI-211) (C$_{29}$H$_{60}$NO$_7$PS) was 597.8280.

The mass spectrum performed using Electrospray Ionization Mass Spectrometry (ES$^-$MS) showed a molecular ion with m/z=596, corresponding to the deprotonated molecular ion [M-H]$^-$. The mass spectrometry spectrum is thus in agreement with the chemical structure of 1-hexadecyl-2-(4-carboxy)butyl-sn-glycero-3-thiophosphorylcholine.

Example 2

Effect of Oxidized Thiophospholipids on in Tyrosine Phosphorylation

Phosphorylation by protein kinases is the most widespread and well-studied signaling mechanism in eukaryotic cells. Phosphorylation can regulate almost every property of a protein and is involved in all fundamental cellular processes. An in vitro assay of tyrosine phosphorylation was therefore performed, as described hereinabove in the Materials and Methods section, in order to determine a biological activity of the oxidized thiophospholipids CI-211 and CI-212.

The biologically active oxidized phospholipid CI-201 (1-hexadecyl 2 (4 carboxy)butyl-sn-glycero-3-phosphocholine) has been previously found to alter tyrosine phosphorylation, using the above assay, suggesting this assay is a reliable strategy for determining biological activity.

As shown in FIG. 1, CI-211 and CI-212, as well as the CI-201 positive control, reduced tyrosine phosphorylation levels.

These results indicate that the thiophospholipids CI-211 and CI-212 exhibit a biological activity similar to that of the phospholipid CI-201.

Example 3

In-Vitro Toxicological Evaluation of Oxidized Thiophospholipids

Comparison of the toxicity range with the biological activity range is important for selection of candidate compounds. Hence, the toxicities of thiophospholipid compounds CI-211 and CI-212 were determined in vitro, as described hereinabove in the Materials and Methods section.

The results are shown in Table 1 and Table 2 below. Data are presented as mean±standard deviation. Statistical significance relative to vehicle-treated cells was calculated using Student's t-test; values of p<0.05 were considered statistically significant and marked with an asterisk (*).

TABLE 1

| Macrophage survival rates following incubation with various concentrations of CI-211 | | | | | | |
|---|---|---|---|---|---|---|
| 0 µg/ml | 2 µg/ml | 10 µg/ml | 20 µg/ml | 50 µg/ml | 100 µg/ml | 150 µg/ml |
| 100% | 124.7 ± 11.4% | 111.6 ± 28.8% | 113 ± 15% | 132.8 ± 12.3% | *62.6 ± 12.9% | *6.7 ± 2.4% |
| 100% | 113.2 ± 7% | 118.4 ± 4.2% | 140.6 ± 11.6% | 132.7 ± 23.2% | 91.4 ± 23.1% | *37.8 ± 5.3% |
| 100% | 90.4 ± 22.4% | 127.9 ± 11.5% | 100.7 ± 22.6% | *69 ± 14.6% | *50.1 ± 11.5% | *22.9 ± 4.3% |

TABLE 2

| Macrophage survival rates following incubation with various concentrations of CI-212 | | | | | | |
|---|---|---|---|---|---|---|
| 0 µg/ml | 2 µg/ml | 10 µg/ml | 20 µg/ml | 50 µg/ml | 100 µg/ml | 150 µg/ml |
| 100% | 98.7 ± 10.3% | 107.1 ± 11.8% | 90.6 ± 21.4% | 71.4 ± 11.4% | *37.6 ± 2.8% | *5.9 ± 3.6% |
| 100% | 77.5 ± 5.5% | 128.5. ± 39.3% | 75.6 ± 9.5% | 55.1 ± 18.9% | *41.7 ± 13.7% | *26.3 ± 18% |
| 100% | 80.8 ± 31% | 84.9 ± 35.7% | 97.5 ± 36.4% | 97.1 ± 48.1% | 95.7 ± 21.3% | *26.2 ± 4.9% |

As shown in Table 1, statistically significant reductions in cell numbers were observed at a dose of 50 µg/ml CI-211 in one experiment, at a dose of 100 µg/ml CI-211 in two experiments and at a dose of 150 µg/ml CI-211 in all three experiments.

As shown in Table 2, statistically significant reductions in cell numbers were observed at a dose of 100 µg/ml CI-212 in two experiments and at dose of 150 µg/ml CI-212 in all three experiments.

The above results indicate that the LD$_{50}$ of CI-211 is above 100 µg/ml (167 µM), and that the LD$_{50}$ of CI-212 is above 50 µg/ml (90 µM).

Example 4

Effect of Oxidized Thiophospholipid on In-Vitro IL12/23p40 Production by Activated Bone Marrow Derived Cells (BMDCs)

The effect of 1, 2.5, 5, 10 or 20 μg/ml CI-211 on in vitro IL12/23p40 production by activated BMDCs was determined as described hereinabove in the Materials and Methods section. CI-211 is non-toxic at these concentrations, as shown in Example 3.

As shown in FIG. 2, CI-211 at concentrations of 1 to 20 μg/ml decreased IL12/23p40 secretion by peptidoglycan-activated BMDCs in a dose dependent manner.

These results indicate that CI-211 is effective at reducing IL12/23p40 production at non-toxic doses.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A compound having formula III:

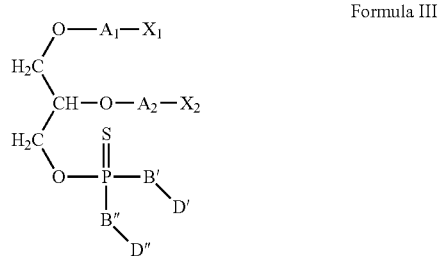

Formula III wherein:
each of $A_1$ and $A_2$ is independently selected from the group consisting of CR"R''', C=O and C=S;
each of B' and B'' is independently selected from the group consisting of sulfur and oxygen;
each of D' and D'' is independently selected from the group consisting of hydrogen, substituted or unsubstituted alkyl, substituted or unsubstituted cycloalkyl, phosphonate and thiophosphonate; and
each of $X_1$ and $X_2$ is independently a saturated or unsaturated hydrocarbon having the general formula II:

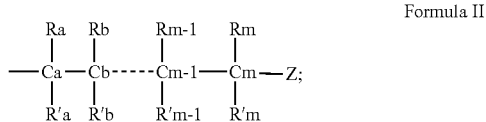

Formula II wherein:
m is an integer of 3-26; and
Z is selected from the group consisting of:

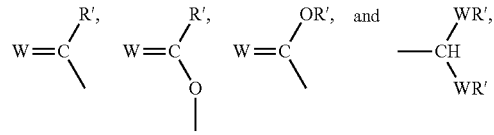

wherein:
W is selected from the group consisting of oxygen, sulfur, nitrogen and phosphorus, whereby each of said nitrogen and phosphorus is substituted by at least one substituent selected from the group consisting of hydrogen, lone pair electrons, alkyl, halo, cycloalkyl, aryl, hydroxy, thiohydroxy, alkoxy, aryloxy, thioaryloxy, thioalkoxy and oxo;
R' is selected from the group consisting of hydrogen, alkyl, cycloalkyl, aryl and heteroaryl; and
at least one Z is not hydrogen;
and wherein:
each of R'' and R''' and each of Ra, R'a, Rb, R'b, to Rm−1, R'm−1, Rm and R'm is independently selected from the group consisting of hydrogen, alkyl, alkenyl, alkylnyl, cycloalkyl, aryl, heteroaryl, heteroalicyclic, halo, trihalomethyl, hydroxy, alkoxy, aryloxy, thiohydroxy, thioalkoxy, thioaryloxy, phosphonate, thiophosphonate, phosphate, thiophosphate, phosphinyl, sulfonyl, sulfinyl, sulfonamide, amide, carbonyl, thiocarbonyl, C-carboxy, O-carboxy, O-carbamate, N-carbamate, C-thiocarboxy, S-thiocarboxy and amino, or, alternatively, at least two of Ra, R'a, Rb, R'b, to Rm−1, R'm−1, Rm and R'm form at least one four-, five- or six-membered aromatic, heteroaromatic, alicyclic or heteroalicyclic ring, or a pharmaceutically acceptable salt, a hydrate or a solvate thereof.

2. The compound of claim 1, wherein at least one of $A_1$ and $A_2$ is CR"R'''.

3. The compound of claim 2, wherein $A_2$ is CR"R'''.

4. The compound of claim 2, wherein each of $A_1$ and $A_2$ is CR"R'''.

5. The compound of claim 1, wherein $X_2$ comprises a Z different than hydrogen.

6. The compound of claim 5, wherein said Z is selected from the group consisting of

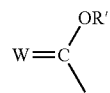

and

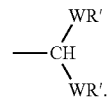

7. The compound of claim 6, wherein W is oxygen and each R' is independently selected from the group consisting of hydrogen and alkyl.

8. The compound of claim 1, wherein:
B' and B" are each oxygen;
D" is hydrogen;
D' is selected from the group consisting of 2-aminoethyl and N,N,N-trimethyl-2-aminoethyl; and
each of $X_1$ and $X_2$ is a saturated hydrocarbon having the general formula II:

$$\begin{array}{ccccc} Ra & Rb & & Rm\text{-}1 & Rm \\ | & | & & | & | \\ -Ca-Cb & ----- & Cm\text{-}1-Cm-Z; \\ | & | & & | & | \\ R'a & R'b & & R'm\text{-}1 & R'm \end{array}$$

Formula II wherein:
m is an integer of 3-15; and
Z is selected from the group consisting of:
H and $$W=C \begin{matrix} OR', \\ \diagdown \end{matrix}$$

wherein:
W is oxygen; and
at least one Z is not hydrogen; and
each of R', Ra, Ra, Rb, R'b, to Rm−1, R'm−1, Rm and R'm is hydrogen.

9. A compound being 1-hexadecyl-2-(4-carboxyl)butyl-sn-glycero-3-thiophosphorylcholine, and having formula IV:

Formula IV or a pharmaceutically acceptable salt thereof.

10. A compound being 1-hexadecyl-2-(4-carboxyl)butyl-sn-glycero-3-O-thiophosphorylethanolamine, and having formula V:

Formula V or a pharmaceutically acceptable salt thereof.

11. The compound of claim 1, being 1-hexadecyl-2-(4-carboxyl)butyl-glycero-3-thiophosphorylcholine, or a pharmaceutically acceptable salt thereof.

12. The compound of claim 1, being 1-hexadecyl-2-(4-carboxyl)butyl-glycero-3-O-thiophosphorylethanolamine, or a pharmaceutically acceptable salt thereof.

13. A pharmaceutical composition comprising, as an active ingredient, the compound of claim 1 and a pharmaceutically acceptable carrier.

14. The pharmaceutical composition of claim 13, packaged in a material and identified in print, in or on said packaging material, for use in the treatment or prevention of an inflammation.

15. The pharmaceutical composition of claim 13, packaged in a packaging material and identified in print, in or on said packaging material, for decreasing of a level of a cytokine selected from the group consisting of interleukin-12 and interleukin 23.

16. A method of treating or preventing an inflammation, the method comprising administering to a subject in need thereof a therapeutically effective amount of a compound of claim 1, thereby treating or preventing the inflammation in said subject.

17. A method of decreasing a level of a cytokine selected from the group consisting of interleukin-12 and interleukin 23 in a subject, the method comprising administering to the subject an effective amount of a compound of claim 1.

18. The composition of claim 14, wherein said inflammation is associated with a disease or disorder selected from the group consisting of an idiopathic inflammatory disease or disorder, a chronic inflammatory disease or disorder, an acute inflammatory disease or disorder, an autoimmune disease or disorder, an infectious disease or disorder, an inflammatory malignant disease or disorder, an inflammatory transplantation-related disease or disorder, an inflammatory degenerative disease or disorder, a disease or disorder associated with a hypersensitivity, an inflammatory cardiovascular disease or disorder, an inflammatory cerebrovascular disease or disorder, a peripheral vascular disease or disorder, an inflammatory glandular disease or disorder, an inflammatory gastrointestinal disease or disorder, an inflammatory cutaneous disease or disorder, an inflammatory hepatic disease or disorder, an inflammatory neurological disease or disorder, an inflammatory musculo-skeletal disease or disorder, an inflammatory renal disease or disorder, an inflammatory reproductive disease or disorder, an inflammatory systemic disease or disorder, an inflammatory connective tissue disease or disorder, an inflammatory tumor, necrosis, an inflammatory implant-related disease or disorder, an inflammatory aging process, an immunodeficiency disease or disorder and an inflammatory pulmonary disease or disorder.

19. The method of claim 16, wherein said inflammation is associated with a disease or disorder selected from the group consisting of an idiopathic inflammatory disease or disorder, a chronic inflammatory disease or disorder, an acute inflammatory disease or disorder, an autoimmune disease or disorder, an infectious disease or disorder, an inflammatory malignant disease or disorder, an inflammatory transplantation-related disease or disorder, an inflammatory degenerative disease or disorder, a disease or disorder associated with a hypersensitivity, an inflammatory cardiovascular disease or disorder, an inflammatory cerebrovascular disease or disorder, a peripheral vascular disease or disorder, an inflammatory glandular disease or disorder, an inflammatory gastrointestinal disease or disorder, an inflammatory cutaneous disease or disorder, an inflammatory hepatic disease or disorder, an inflammatory neurological disease or disorder, an inflammatory musculo-skeletal disease or disorder, an inflammatory renal disease or disorder, an inflammatory reproductive disease or disorder, an inflammatory systemic disease or disorder, an inflammatory connective tissue disease or disorder, an inflammatory tumor, necrosis, an inflammatory implant-related disease or disorder, an inflammatory aging process, an immunodeficiency disease or disorder and an inflammatory pulmonary disease or disorder.

20. A method of introducing a thiophosphate moiety into a compound so as to produce the compound of claim 1, the method comprising:

reacting a thiophosphorus-containing compound having a second reactive group and a third reactive group with a compound having the general formula VI:

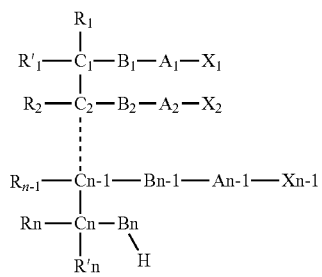

Formula VI wherein:

n is an integer of 1-6, whereas if n=1, Cn, Rn and R'n are absent, and $C_1$ is attached to Bn;

each of $B_1$, $B_2$, to Bn−1 and Bn is independently selected from the group consisting of oxygen, sulfur, nitrogen, phosphorus and silicon, whereby each of said nitrogen, phosphorus and silicon is substituted by at least one substituent selected from the group consisting of hydrogen, lone pair electrons, alkyl, halo, cycloalkyl, aryl, hydroxy, thiohydroxy, alkoxy, aryloxy, thioaryloxy, thioalkoxy and oxo;

each of $A_1$, $A_2$, to An−1 is independently selected from the group consisting of CR"R'", C=O and C=S; and each of $X_1$, $X_2$, to Xn−1 is independently a saturated or unsaturated hydrocarbon having the general formula II:

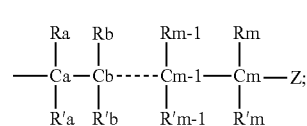

Formula II wherein:
m is an integer of 1-26; and
Z is selected from the group consisting of:
H,

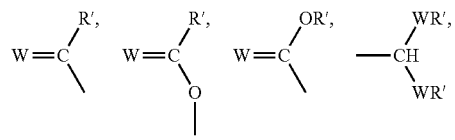

and a pre-oxidized moiety,
whereas:
W is selected from the group consisting of oxygen, sulfur, nitrogen and phosphorus, whereby each of said nitrogen and phosphorus is substituted by at least one substituent selected from the group consisting of hydrogen, lone pair electrons, alkyl, halo, cycloalkyl, aryl, hydroxy, thiohydroxy, alkoxy, aryloxy, thioaryloxy, thioalkoxy and oxo;
R' is selected from the group consisting of hydrogen, alkyl, cycloalkyl, aryl and heteroaryl; and
at least one Z is not hydrogen;
and wherein:
each of $R_1$, $R'_1$, $R_2$, to Rn−1, Rn, R'n, each of R" and R'" and each of Ra, R'a, Rb, R'b, to Rm−1, R'm−1, Rm and R'm is independently selected from the group consisting of hydrogen, a bond, alkyl, alkenyl, alkylnyl, cycloalkyl, aryl, heteroaryl, heteroalicyclic, halo, trihalomethyl, hydroxy, alkoxy, aryloxy, thiohydroxy, thioalkoxy, thioaryloxy, phosphonate, thiophosphonate, phosphate, thiophosphate, phosphinyl, sulfonyl, sulfinyl, sulfonamide, amide, carbonyl, thiocarbonyl, C-carboxy, O-carboxy, O-carbamate, N-carbamate, C-thiocarboxy, S-thiocarboxy and amino, or, alternatively, at least two of $R_1$, $R'_1$, R2, to Rn−1, Rn and R'n and/or at least two of Ra, R'a, Rb, R'b, to Rm−1, R'm−1, Rm and R'm form at least one four-, five- or six-membered aromatic, heteroaromatic, alicyclic or heteroalicyclic ring; and
each of $C_1$, $C_2$, to Cn−1, Cn, and each of Ca, Cb, to Cm−1 and Cm is a chiral or non-chiral carbon atom, whereby each chiral carbon atom has a S-configuration and/or a R-configuration,
or a pharmaceutically acceptable salt, a hydrate or a solvate thereof,
said second reactive group being capable of reacting with said Bn, to thereby provide a compound having a reactive thiophosphorus-containing group attached to said Bn; and
converting said reactive thiophosphorus-containing group to said thiophosphate moiety, thereby producing the compound of claim 1,
wherein when Z in said Formula VI is said pre-oxidized moiety, the method further comprises oxidizing said pre-oxidized moiety.

21. The method of claim 20, wherein Bn is selected from the group consisting of oxygen and sulfur.

22. The method of claim 20, wherein said pre-oxidized moiety is an unsaturated alkyl.

23. The method of claim 20, wherein said thiophosphorus-containing compound is $PSCl_3$.

24. The method of claim 20, wherein said reacting is performed in the presence of a base.

25. The method of claim 24, wherein said base is a tertiary amine.

26. The method of claim 23, wherein said reactive thiophosphorus-containing group is a dichlorothiophosphate group.

27. The method of claim 20, wherein said compound having the general formula VI has said saturated or unsaturated hydrocarbon having the general formula II attached thereto via an ether bond.

28. The method of claim 20, wherein said thiophosphate moiety is thiophosphoric acid and said converting comprises hydrolyzing said reactive thiophosphorus-containing group.

29. The method of claim 20, wherein said thiophosphate moiety comprises an alkylamino group and said converting comprises reacting said reactive thiophosphorus-containing moiety with a derivative of an aminoalkyl, said derivative being capable of reacting with said reactive thiophosphorus-containing group.

30. The compound of claim 6, wherein said Z is $$W=C\begin{matrix}OR'\\ \\ \end{matrix}.$$

31. The compound of claim 1, wherein B' and B" are each oxygen.

32. The compound of claim 1, wherein D" is hydrogen.

33. The compound of claim 1, wherein D' is amino-substituted alkyl.

34. The compound of claim 1, wherein D' is selected from the group consisting of 2-aminoethyl and N,N,N-trimethyl-2-aminoethyl.

35. The compound of claim 1, wherein:

B' and B" are each oxygen;

D" is hydrogen; and

D' is selected from the group consisting of 2-aminoethyl and N,N,N-trimethyl-2-aminoethyl.

* * * * *